(12) United States Patent
Blanpied et al.

(10) Patent No.: US 9,915,626 B2
(45) Date of Patent: Mar. 13, 2018

(54) DISCRIMINATION OF LOW-ATOMIC WEIGHT MATERIALS USING SCATTERING AND STOPPING OF COSMIC-RAY ELECTRONS AND MUONS

(71) Applicant: Decision Sciences International Corporation, Poway, CA (US)

(72) Inventors: Gary Blanpied, Ramona, CA (US); Sankaran Kumar, San Marcos, CA (US); Dustin Dorroh, Ramona, CA (US); Craig Morgan, El Cajon, CA (US); Michael James Sossong, Ramona, CA (US)

(73) Assignee: Decision Sciences International Corporation, Poway, CA (US)

( * ) Notice: Subject to any disclaimer, the term of this patent is extended or adjusted under 35 U.S.C. 154(b) by 0 days.

(21) Appl. No.: 14/633,020

(22) Filed: Feb. 26, 2015

(65) Prior Publication Data

US 2015/0241593 A1     Aug. 27, 2015

Related U.S. Application Data

(60) Provisional application No. 61/945,061, filed on Feb. 26, 2014, provisional application No. 62/036,050, (Continued)

(51) Int. Cl.
*G01N 23/04* (2006.01)
*G01V 5/00* (2006.01)
*G01N 23/20* (2018.01)

(52) U.S. Cl.
CPC ........... *G01N 23/046* (2013.01); *G01N 23/20* (2013.01); *G01V 5/0016* (2013.01); *G01V 5/0091* (2013.01); *G01N 2223/05* (2013.01)

(58) Field of Classification Search
CPC .... G01V 5/0025; G01V 5/005; G01V 5/0016; G01V 5/0091; G01N 23/046
See application file for complete search history.

(56) References Cited

U.S. PATENT DOCUMENTS 7,945,105 B1 *   5/2011   Jaenisch .............. G01V 5/0008
                                                                       382/128
8,247,767 B2      8/2012   Morris et al.
(Continued)

FOREIGN PATENT DOCUMENTS

WO       2014/051895 A2    4/2014
WO       2016/025409 A1    2/2016

OTHER PUBLICATIONS

Agostinelli, S., et al., "GEANT4—a simulation tool kit," Nuclear Instruments and Methods in Physics Research A, 506(3)250-303, Jul. 2003.
(Continued)

*Primary Examiner* — Jason McCormack
*Assistant Examiner* — Sean Luck
(74) *Attorney, Agent, or Firm* — Perkins Coie LLP

(57) ABSTRACT

Techniques, systems, and devices are disclosed for constructing a scattering and stopping relationship of cosmic-ray charged particles (including cosmic-ray electrons and/or cosmic-ray muons) over a range of low-atomic-mass materials, and to detect and identify content of a volume of interest (VOI) exposed to cosmic-ray charged particles based on the constructed scattering and stopping relationship. In one aspect, a process for constructing a scattering-stopping relationship for a range of low-density materials exposed to cosmic-ray charged particles is disclosed. This technique first determines a scattering parameter and a stopping parameter for each material within the range of low-density materials exposed to charged particles from cosmic ray. The technique then establishes a scattering-
(Continued)

stopping relationship of cosmic ray charged particles for the range of low-density materials based on the determined pairs of scattering and stopping parameters associated with the range of low-density materials.

25 Claims, 20 Drawing Sheets

Related U.S. Application Data filed on Aug. 11, 2014, provisional application No. 62/075,788, filed on Nov. 5, 2014.

(56) References Cited

U.S. PATENT DOCUMENTS

| | | | | |
|---|---|---|---|---|
| 8,275,567 | B2* | 9/2012 | Lightfoot | G01T 1/167 250/252.1 |
| 8,536,527 | B2 | 9/2013 | Morris et al. | |
| 8,575,546 | B2 | 11/2013 | Nagamine | |
| 2008/0191133 | A1* | 8/2008 | Morris | G01N 23/20 250/307 |
| 2008/0315091 | A1* | 12/2008 | Morris | G01T 1/18 250/307 |
| 2010/0310036 | A1* | 12/2010 | Burleton | A61B 6/405 378/5 |
| 2011/0127436 | A1* | 6/2011 | Hashizume | G01T 1/1611 250/363.04 |
| 2011/0135180 | A1* | 6/2011 | Sugrue | G06T 5/50 382/131 |
| 2011/0216945 | A1* | 9/2011 | Jaenisch | G01V 5/0008 382/104 |
| 2011/0248163 | A1* | 10/2011 | Morris | G01N 23/046 250/307 |
| 2014/0319365 | A1 | 10/2014 | Sossong et al. | |
| 2016/0041297 | A1 | 2/2016 | Blanpied et al. | |

OTHER PUBLICATIONS

Allison, J., et al., "Geant4 Developments and Applications," IEEE Transactions on Nuclear Science, 53(1):270-278, Feb. 2006.

Beringer, J., et al., "Cosmic Rays," Particle Data Group, Physical Review D, 86(1):1-21, Jun. 2012 [accessed at http://pdg.lbl.gov/2012/reviews/rpp2012-rev-cosmic-rays.pdf ].

Beringer, J., et al., "Passage of particles through matter" Particle Data Group, Physical Review D, 86(1):1-42, Jun. 2012 [accessed at http://pdg.lbl.gov/2013/reviews/rpp2012-rev-passage-particles-matter.pdf].

Borozdin, K. N., et al., "Surveillance: Radiographic Imaging with Cosmic Ray Muons," Nature, 422:277-278, Mar. 2003.

Grimani, C., et al., "Measurements of the absolute energy spectra of cosmic-ray positrons and electrons above 7 GeV," Astronomy and Astrophysics, 392(1):287-294, Sep. 2002.

International Search Report and Written Opinion dated Nov. 12, 2015 for International Application No. PCT/US2015/044531, filed on Aug. 10, 2015 (8 pages).

International Search Report and Written Opinion dated Nov. 27, 2015 for International Application No. PCT/US2015/017846, filed on Feb. 26, 2015 (7 pages).

Morris, C.L., et al., "Tomographic Imaging with Cosmic Ray Muons," Science & Global Security, 16(1-2):37-53, Oct. 2008.

Morris, C.L., et al., "Obtaining material identification with cosmic ray radiography," arXiv:1210.6102, 10 pages, Oct. 2012 [retrieved on Oct. 10, 2015] <URL: http://arxiv.org/abs/1210.6102>.

* cited by examiner

DISCRIMINATION OF LOW-ATOMIC WEIGHT MATERIALS USING SCATTERING AND STOPPING OF COSMIC-RAY ELECTRONS AND MUONS

CROSS REFERENCE TO RELATED APPLICATIONS

This patent document claims the benefit of priority of U.S. Provisional Patent Application No. 61/945,061, filed on Feb. 26, 2014; U.S. Provisional Patent Application No. 62/036,050, filed on Aug. 11, 2014; and U.S. Provisional Patent Application No. 62/075,788, filed on Nov. 5, 2014. The entire content of the before-mentioned patent applications is incorporated by reference as part of the disclosure of this document.

TECHNICAL FIELD

The subject matter described in this disclosure generally relates to systems, devices, and processes for imaging and sensing based on cosmic-ray tomography. More specifically, the disclosed technology provides a technique for applying cosmic-ray tomography in a manner that can detect and characterize not only dense assemblages of heavy nuclei but also assemblages of medium- and light-atomic-mass materials.

BACKGROUND

Cosmic ray imaging and sensing are techniques which exploit the multiple Coulomb scattering of highly penetrating cosmic ray-produced charged particles such as muons to perform non-destructive inspection of the material without the use of artificial radiation. The Earth is continuously bombarded by energetic stable charged particles, mostly protons, coming from deep space. These charged particles interact with atoms in the upper atmosphere to produce showers of charged particles that include many short-lived pions which decay producing longer-lived muons. Muons interact with matter primarily through the Coulomb force having no nuclear interaction and radiating much less readily than electrons. Such cosmic ray-produced charged particles slowly lose energy through electromagnetic interactions. Consequently, many of the cosmic ray produced muons arrive at the Earth's surface as highly penetrating charged radiation. The muon flux at sea level is about 1 muon per $cm^2$ per minute.

SUMMARY

Techniques, systems, and devices are disclosed for constructing a scattering and stopping relationship of cosmic-ray electrons and muons over a range of low-atomic-mass materials, and to detect and identify contents of a VOI exposed to cosmic ray produced charged particles including electrons and muons based on the constructed scattering and stopping relationship.

In one aspect, a process for constructing a scattering-stopping relationship for a range of low-density materials exposed to cosmic-ray charged particles is disclosed. The process includes determining a scattering parameter and a stopping parameter for a given material within a range of low-density materials exposed to charged particles from cosmic ray. The process includes creating a VOI of the material. The process includes for the VOI inside a cosmic ray detector, determining a scattering parameter of cosmic ray charged particles interacting with the VOI of the material to represent a set of cosmic ray charged particles entering and exiting the VOI. The process includes determining a stopping parameter of cosmic ray charged particles interacting with the VOI of the material to represent a set of cosmic ray charged particles entering and stopping inside the VOI. The process includes establishing a scattering-stopping relationship of cosmic ray charged particles for the range of low-density materials based on the determined pairs of scattering and stopping parameters associated with the range of low-density materials.

In some implementations, the process includes creating the VOI of the material by placing the material inside a common container.

In some implementations, the common container can include one of a shipping container; a vehicle; or a package.

In some implementations, the process includes determining an effect of the common container by separately measuring scattering and stopping parameters of cosmic ray charged particles interacting with the common container when the common container is empty.

In some implementations, the material in the range of low-density materials has a density substantially equal to or less than density of aluminum.

In some implementations, the values of the pairs of scattering and stopping parameters increase substantially monotonically with the densities of the range of low-density materials.

In some implementations, the process includes determining the scattering parameter of charged particles by using a cosmic ray based detection system. The cosmic ray based detection system includes a first set of position sensitive cosmic ray charged particle detectors located on a first location with respect to the VOI to detect events of incident cosmic ray charged particles that penetrate the first set of position sensitive cosmic ray charged particle detectors and enter the VOI. The cosmic ray based detection system includes a second set of position sensitive cosmic ray charged particle detectors located on a location with respect to the VOI and opposite to the first location to detect events of outgoing cosmic ray charged particles exiting the VOI. The cosmic ray based detection system includes a signal processing unit to receive signals of the incident cosmic ray charged particles from the first set of position sensitive cosmic ray charged particle detectors and signals of the outgoing cosmic ray charged particles from the second set of position sensitive cosmic ray charged particle detectors. The signal processing unit can determine the scattering parameter based at least on the received signals of the outgoing cosmic ray charged particles.

In some implementations, the detection process can include determining the stopping parameter of cosmic ray charged particles by using received signals of the incident cosmic ray charged particles from the first set of position sensitive cosmic ray charged particle detectors to determine a number of incident cosmic ray charged particles and using received signals of the outgoing cosmic ray charged particles from the second set of position sensitive cosmic ray charged particle detectors to determine a number of scattered cosmic ray charged particles. The process includes computing a raw number of stopped cosmic ray charged particles by subtracting the number of scattered cosmic ray charged particles from the number of incident cosmic ray charged particles.

In some implementations, the process can include correcting the raw number of stopped cosmic ray charged particles to compensate for effects of the placement location of the VOI inside the cosmic ray detector. A placement location near an edge of the cosmic ray detector can tend to overestimate the raw number of stopped cosmic ray charged particles due to an increasing number of undetected scattered cosmic ray charged particles by the position sensitive cosmic ray charged particle detector.

In some implementations, the process can include compensating for the effects of the placement location of the VOI by dividing the raw number of stopped cosmic ray charged particles by the determined number of scattered cosmic ray charged particles to normalize for variations in detection efficiency at different locations of the position sensitive cosmic ray charged particle detector.

In some implementations, the process includes correcting the raw number of stopped charged particles to compensate for effects of a sample property, such as a thickness of the VOI or an average path length through the material in the VOI.

In some implementations, the process includes correcting the determined scattering and stopping parameters to compensate for a geometric effect of the VOI.

In some implementations, the cosmic ray charged particles include cosmic-ray electrons and/or cosmic-ray muons.

In another aspect, a process for identifying contents of a VOI exposed to cosmic-ray charged particles includes determining a number of scattered cosmic ray charged particles from incident cosmic ray charged particles interacting with the VOI. The process includes determining a number of stopped cosmic ray charged particles from incident cosmic ray charged particles interacting with the VOI. The process includes comparing the determined numbers of scattered and stopped cosmic ray charged particles against an established scattering-stopping relationship of cosmic ray charged particles obtained for a range of low-density materials exposed to cosmic-ray charged particles to determine whether the contents of the VOI match a material in the range of low-density materials.

In some implementations, the VOI is placed inside a container.

In some implementations, the container can include one of a shipping container, a vehicle, or a package.

In some implementations, the process includes correcting for an effect of the container on the determined numbers of scattered and stopped cosmic ray charged particles.

In some implementations, the process includes determining the number of scattered cosmic ray charged particles by using a cosmic ray charged particle detection system. The cosmic ray charged particle detection system includes a first set of position sensitive cosmic ray charged particle detectors located on a first location with respect to the VOI to detect events of incident cosmic ray charged particles that penetrate the first set of position sensitive cosmic ray charged particle detectors and enter the VOI. The system includes a second set of position sensitive cosmic ray charged particle detectors located on a second location with respect to the VOI and opposite to the first location to detect events of outgoing cosmic ray charged particles exiting the VOI. The system includes a signal processing unit to receive signals of the incident cosmic ray charged particles from the first set of position sensitive cosmic ray charged particle detectors and signals of the outgoing cosmic ray charged particles from the second set of position sensitive cosmic ray charged particle detectors. The signal processing unit can determine the number of scattered cosmic ray charged particles based at least on the received signals of the outgoing cosmic ray charged particles.

In some implementations, the process includes determining the number of stopped cosmic ray charged particles by using received signals of the incident cosmic ray charged particles from the first set of position sensitive cosmic ray charged detectors to determine a number of incident cosmic ray charged particles. The process can include computing a raw number of stopped cosmic ray charged particles by subtracting the determined number of scattered cosmic ray charged particles from the determined number of incident cosmic ray charged particles.

In some implementations, the process further includes correcting the raw number of stopped cosmic ray charged particles to compensate for effects of the placement location of the VOI inside the cosmic ray charged particle detector system. A placement location near an edge of the cosmic ray detector may tend to overestimate the raw number of stopped cosmic ray charged particles due to an increasing number of undetected scattered cosmic ray charged particles by the cosmic ray detector system.

In some implementations, the system includes compensating for the effects of the placement location of the VOI by dividing the raw number of stopped cosmic ray charged particles by the determined number of scattered cosmic ray charged particles to normalize for variations in detection efficiency at different locations of the cosmic ray detector system.

In some implementations, the process includes correcting the raw number of stopped cosmic ray charged particles to compensate for effects of a sample property including a thickness of the VOI. In some implementations, the process includes correcting the raw number of stopped cosmic ray charged particles to compensate for effects of a sample property including an average path length through the material in the sample.

In some implementations, the process includes correcting the determined scattering and stopping parameters to compensate for a geometric effect of the VOI.

In some implementations, the process includes using the determined number of stopped cosmic ray charged particles to estimate a thickness of the VOI. In some implementations, an average path length through the material in the VOI can be determined to normalize the stopping power of the material in the VOI.

In some implementations, the process includes classifying the contents of the VOI as a low density material when the determined numbers of scattered and stopped cosmic ray charged particles fall within an established scattering-stopping relationship for the range of low-density materials.

In some implementations, the aforementioned cosmic ray charged particles include cosmic-ray electrons and/or cosmic-ray muons.

In yet another aspect, a detection system for detecting and identifying contents of a VOI exposed to cosmic-ray charged particles includes a first set of position sensitive cosmic ray charged particle detectors at a first location with respect to the VOI to detect events of incident cosmic ray charged particles that penetrate the first set of position sensitive cosmic ray charged particle detectors and enter the VOI. The detection system includes a second set of position sensitive cosmic ray charged particle detectors at a second location with respect to the VOI and opposite to the first location to detect events of outgoing cosmic ray charged particles exiting the VOI. The detection system includes a signal processing unit that receives signals of the incident cosmic ray charged particles from the first set of position sensitive cosmic ray charged particle detectors and signals of the outgoing cosmic ray charged particles from the second set of position sensitive cosmic ray charged detectors, the signal processing unit is configured to determine a number of scattering cosmic ray charged particles and a number of stopping charged cosmic ray particles by the VOI based on the received signals of the incident cosmic ray charged particles and the outgoing cosmic ray charged particles.

In some implementations, the signal processing unit can determine a number of incident cosmic ray charged particles based on the received signals of the incident cosmic ray charged particles from the first set of position sensitive cosmic ray charged particle detectors. The signal processing unit can determine a number of scattered cosmic ray charged particles based on the received signals of the outgoing cosmic ray charged particles. The signal processing unit can compute a raw number of stopped cosmic ray charged particles by subtracting the determined number of scattered cosmic ray charged particles from the determined number of incident cosmic ray charged particles.

In some implementations, the signal processing unit can correct the raw number of stopped cosmic ray charged particles to compensate for undetected scattered cosmic ray charged particles by normalizing the raw number of stopped cosmic ray charged particles by the number of scattered cosmic ray charged particles.

In some implementations, the first set and second set of position sensitive cosmic ray charged particle detectors include a set of drift tubes.

In some implementations, the first set and second set of position sensitive cosmic ray charged particle detectors includes a set of drift tubes which can be used to detect both cosmic-ray muons and cosmic-ray electrons.

In some implementations, the cosmic ray charged particles include cosmic-ray electrons and/or cosmic-ray muons.

DETAILED DESCRIPTION

Figure 1:
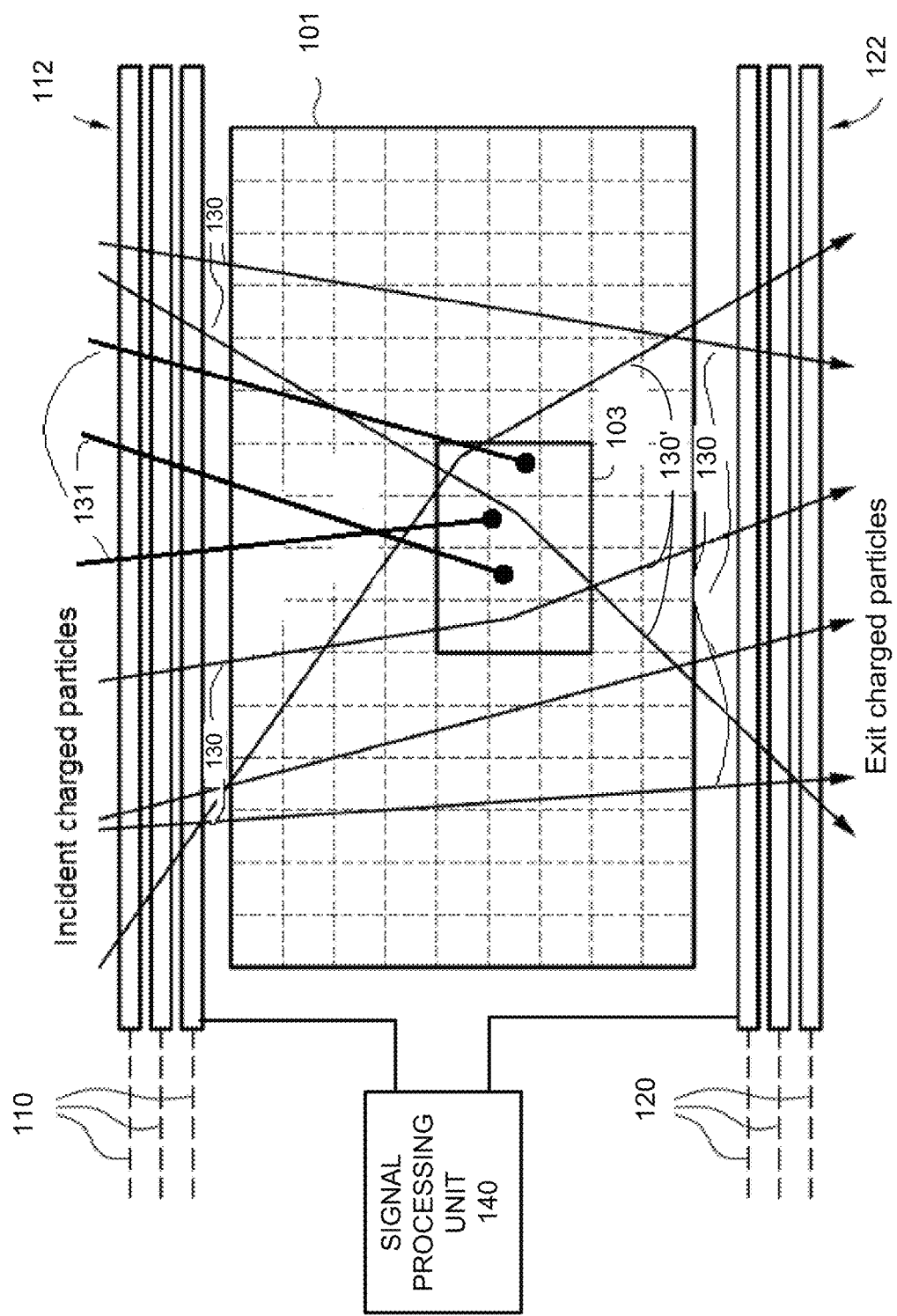
FIG. 1 shows an exemplary cosmic-ray particle tomography system in accordance with some embodiments described herein.

As a muon moves through a material, Coulomb scattering off of the charges of sub-atomic particles perturb the muon's trajectory. The total deflection depends on several material properties, but the dominant effects are the atomic number, Z, of nuclei and the density of the material. The trajectories of muons are more strongly affected by materials that make good gamma ray shielding, such as lead and tungsten, and by special nuclear materials (SNM), such as uranium and plutonium, than by materials that make up more ordinary objects such as water, plastic, aluminum and steel. Each muon carries information about the materials that the muon has penetrated. The scattering of multiple muons can be measured and processed to probe the properties of the penetrated materials. A material with a high atomic number Z and a high density can be detected and identified when the material is located, inside low-Z and medium-Z matter.

In addition to muons, cosmic rays also generate electrons. Electrons are less massive and generally have lower momenta than muons and hence scatter more in a given material. Due to their larger scattering, electrons can be used to differentiate materials particularly those with low to medium Z and densities that may not significantly scatter muons.

Coulomb scattering from atomic nuclei in matter results in a very large number of small angle deflections of charged particles as they transit the matter. In some examples, a correlated distribution function can be used to approximately characterize the displacement and angle change of the trajectory that depends on the density and the atomic charge of the material. As an example, this distribution function can be approximated as a Gaussian distribution. The width of the distribution function is proportional to the inverse of the momentum of the charged particle and the square root of the real density of material measured in radiation lengths. The correlated distribution function of cosmic ray-produced particles (e.g., muons and electrons) can provide information on materials in the paths of the particles with no radiation dose above the Earth's background and proper detection of such cosmic ray-produced particles can be implemented in a way that is especially sensitive to selected materials to be detected such as good radiation shielding materials.

In some examples of cosmic ray imaging and sensing, a muon tomography system can perform tomography of a volume or region under inspection based on scattering of cosmic ray particles by certain target materials in the volume or region. For example, cosmic ray tomography systems can be used for detecting certain targeted materials, e.g., such as materials that can be used to threaten the public, including smuggled nuclear materials. Cosmic ray tomography detector systems can be used jointly with or as an alternative to other nuclear material detectors such as gamma or X-ray detectors. Gamma and X-ray detectors operate by directing Gamma and X-ray radiation to a target material in the volume or region of interest and measuring penetrated Gamma and X-ray radiation. Shielding of nuclear materials can reduce the count rates in the Gamma and X-ray detectors and reduce the detection performance of Gamma and X-ray detectors. Cosmic ray tomography detection systems can detect shielded nuclear materials and objects.

An exemplary cosmic ray charged particle tomography detection system can include cosmic ray charged particle detectors to detect and track ambient cosmic ray produced charged particles, such as muons and electrons traversing through a volume of interest (VOI). The cosmic ray charged particle detectors can include an array of drift-tube sensors to enable tomographic imaging of the VOI. Cosmic ray charged particles, e.g., primarily muons and electrons, shower through the VOI, and measurement of individual particle tracks can be used to reconstruct the three-dimensional distribution of atomic number (Z) and density of materials in the VOI using particle scattering.

Disclosed technology includes techniques, systems, and devices for using position sensitive cosmic ray charged particle detector arrays to construct a scattering and stopping relationship of cosmic-ray charged particles over a wide range of low-atomic-mass materials, and to detect and identify contents of a VOI exposed to cosmic-ray charged particles based on the constructed scattering and stopping relationship for the range of low-atomic-mass materials.

The disclosed technology can be used to apply cosmic-ray tomography in a manner that can detect and characterize not only dense materials (tungsten, lead, uranium) but also medium- and light-atomic-mass materials (such as metal parts, conventional explosives, and other common materials). Characterization may enable discrimination between allowed contents in commerce and contraband (explosives, illegal drugs, cash, and precious metals). In one aspect, the disclosed technology provides for a Multi-Mode Passive Detection System (MMPDS) that uses the muon component of cosmic rays to interrogate VOI. Highly energetic muons pass essentially un-scattered through materials of light atomic mass and are only weakly scattered by conventional metals used in industry. Electrons are appreciably scattered by light elements and stopped by sufficient thicknesses of materials containing medium-atomic-mass elements (mostly metals). The disclosed technology can be used to develop a useful parameter, designated the "Stopping Power" of a sample. The low-density regime, comprising materials up to aluminum, is characterized by very little scattering but a strong variation in stopping power. The medium-to-high density regime shows a larger variation in scattering than in stopping power. The detection of emitted gamma rays is another useful signature of some materials. In determining the stopping power of a given material, an average path length through the material can be determined or the sample thickness estimated.

In another aspect, a process for constructing a scattering-stopping relationship for a range of low-density materials exposed to cosmic-ray charged particles is disclosed. The process includes determining a scattering parameter and a stopping parameter for a given material within the range of low-density materials exposed to charged particles from cosmic ray. The process includes creating a VOI of the material exposed to cosmic ray charged particles. The process includes determining a scattering parameter of charged particles interacting with the VOI of the material exposed cosmic ray charged particles to represent a set of cosmic ray charged particles entering and exiting the VOI. The process includes determining a stopping parameter of cosmic ray charged particles interacting with the VOI to represent a set of cosmic ray charged particles entering and stopping inside the VOI. The process includes establishing a scattering-stopping relationship of cosmic ray charged particles for the range of low-density materials based on the determined pairs of scattering and stopping parameters associated with the range of low-density materials.

In another aspect, a process for identifying a VOI inside a container exposed to cosmic-ray charged particles include determining a number of scattered cosmic ray charged particles interacting with the VOI. The process includes determining a number of stopped cosmic ray charged particles interacting with the VOI. The process includes comparing the determined numbers of scattered and stopped cosmic ray charged particles against an established scattering-stopping relationship of cosmic ray charged particles obtained for a range of low-density materials exposed to cosmic ray charged particles to determine whether the VOI matches a material in the range of low-density materials.

In yet another aspect, a detection system for detecting a VOI inside a container exposed to cosmic ray charged particles include a first set of position sensitive cosmic ray charged particle detectors at a first location with respect to the VOI to detect events of incident cosmic ray charged particles that penetrate the first set of position sensitive cosmic ray charged particle detectors and enter the VOI. The detection system includes a second set of position sensitive cosmic ray charged particle detectors at a second location with respect to the VOI and opposite to the first location to detect events of outgoing cosmic ray charged particles exiting the VOI. The detection system includes a signal processing unit that receives signals of the incident cosmic ray charged particles from the first set of position sensitive cosmic ray charged particle detectors and signals of the outgoing cosmic ray charged particles from the second set of position sensitive cosmic ray charged particle detectors. The signal processing unit can determine a number of scattering cosmic ray charged particles and a number of stopping cosmic ray charged particles by the VOI based on the received signals of the incident cosmic ray charged particles and the outgoing cosmic ray charged particles.

Cosmic ray charged particles (such as electrons and muons) passing through a VOI associated with a matter interact by scattering from the atoms of the matter and by being absorbed by them ("stopping"). A technique relying primarily on the muon component of cosmic rays can be used to interrogate a Volumes of Interest (VOI). Because muons are highly energetic and massive, muons can pass essentially un-scattered through materials of light atomic mass and are typically only weakly scattered by conventional metals used in industry (e.g., aluminum, iron, steel, and the like). Substantial scattering and absorption generally only occur when muons encounter sufficient thicknesses of heavy elements such as lead and tungsten, and special nuclear materials (SNM), such as uranium and plutonium.

Techniques can be implemented to construct relationship between scattering and stopping of cosmic-ray charged particles over a wide range of atomic masses and material densities. Due to the differing behaviors of cosmic ray produced muons and electrons when scattering and stopping in different atomic mass materials, a cosmic ray tomography system can be implemented to use cosmic ray produced muons and electrons to respectively detect medium to high and low atomic-mass materials. For example, the relationship can be obtained for both muons and the lighter, less energetic electrons which are also present in cosmic rays. Electrons can be considerably scattered by low-atomic-mass elements (e.g., carbon, oxygen, etc.) and stopped by sufficient thicknesses of materials containing medium-atomic-mass elements (e.g., metals, etc.). Hence, relationship between scattering and stopping of electrons and/or muons can be constructed over a wide range of low-atomic-mass materials while relationship between scattering and stopping of muons can be constructed over a wide range of medium or high-atomic-mass materials. By combining the scattering and stopping responses of both muons and electrons, the range of material detection and characterization can be extended beyond special nuclear materials (SNM) to cover other types of contraband.

In some implementations, comparison of the stopping and scattering signals in the VOI can allow for the identification of materials in the VOI, and/or for the classification of the materials as low, medium or high density. In addition, the stopping signal can be used to estimate a thickness of the detected material. The presence of clutter in the VOI may distort the signal. However, this distortion may be mitigated by using a mapping of stopping and scattering in the VOI, and the ratio between the stopping and scattering to improve object detection and classification. In some implementations, an average path length through a given material can be used to normalize the comparison of the stopping and scattering signals.

In this disclosure, terms "a low atomic mass material," "a low-atomic-mass material" and "a low density material" can refer to both a material made of a single low-atomic-mass element such as carbon and oxygen, and a compound or a mixture having a low density, such as organic materials, drugs and explosives. Similarly, terms "a medium atomic mass material," "a medium-atomic-mass material" and "a medium density material" can refer to either a material made of a single medium-atomic-mass element such as aluminum and iron, or a compound or a mixture having a medium density, such as steel and some other alloys. Also, terms "a high atomic mass material," "a high-atomic-mass material" and "a high density material" can refer to either a material made of a single high-atomic-mass element such as lead, tungsten, uranium and plutonium, or a compound or a mixture having a high density, such as high density alloys. In some implementations, low density or low atomic mass material refers to any material with density substantially equal to or less than that of aluminum. Therefore, these low density materials can include all organic materials, including but not limited to contraband such as illegal drugs and conventional explosives. The disclosed technology presents the existence of a linear relationship of scattering to stopping for these low density materials.

The cosmic-ray charged particle detection systems, devices and methods described in this application can be implemented to detect presence of certain objects or materials such as nuclear materials and to obtain tomographic information of such objects or materials in various applications including but not limited to inspecting packages, containers, occupied vehicles at security check points, border crossings and other locations for nuclear threat objects that may range from fully assembled nuclear weapons to small quantities of highly shielded nuclear materials. Features described in this application can be used to construct various particle detection systems.

For example, a particle detection system can include an object holding area for placing an object to be inspected, a first set of position sensitive cosmic-ray charged particle detectors at a first location with respect to the object holding area to measure positions and directions of incident or incoming cosmic-ray charged particles entering the object holding area, a second set of position sensitive cosmic-ray charged particle detectors at a second location with respect to the object holding area opposite to the first location to measure positions and directions of outgoing cosmic-ray charged particles exiting the object holding area, and a signal processing unit, which may include, e.g., a microprocessor, to receive data of measured signals associated with the incoming muons from the first set of position sensitive cosmic-ray charged particle detectors and measured signals associated with the outgoing cosmic-ray charged particles from the second set of position sensitive cosmic ray charged particle detectors. As an example, the first and second sets of position sensitive cosmic ray charged particle detectors can be implemented to include drift tubes arranged to allow at least three charged particle positional measurements in a first direction and at least three charged particle positional measurements in a second direction different from the first direction. The signal processing unit can analyze scattering behaviors of the cosmic-ray charged particles caused by scattering of the cosmic-ray charged particles in the materials within the object holding area based on the measured incoming and outgoing positions and directions of cosmic-ray charged particle to obtain a tomographic profile or the spatial distribution of scattering centers within the object holding area.

The obtained tomographic profile or the spatial distribution of scattering centers can be used to reveal the presence or absence of one or more objects or materials in the object holding area such as materials with high atomic numbers including nuclear materials or devices. The first and second position sensitive cosmic ray charged particle detectors can be implemented in various configurations, including drift cells such as drift tubes filled with a gas which can be ionized by muons or electrons. Such a system can be used to utilize naturally occurring cosmic-ray charged particles as the charged particle source for detecting one or more objects in the object holding area.

In applications for portal monitoring, the illustrative embodiments provide an approach to potentially enable robust nuclear material detection at reduced cost and with increased effectiveness. Furthermore, the approach can potentially provide a radiation portal monitor which is capable of determining whether a given vehicle or cargo is free of nuclear threats by both measuring the absence of a potential shielded package and the absence of a radiation signature.

The portal monitoring systems of the illustrative embodiments shown in the accompanying drawings employ cosmic ray-produced charged particle tracking with drift tubes. As will be explained in more detail below, the portal monitoring systems utilize drift tubes to enable tracking of cosmic ray charged particles, such as muons and electrons, passing through a volume as well as detection of gamma rays. Advantageously, these portal monitoring systems can effectively provide the combined function of a cosmic ray radiography apparatus with passive or active gamma radiation counter to provide a robust detector for nuclear threats. This eliminates the need for two separate instruments.

Cosmic ray-produced muons and electrons can provide information with no radiation dose above the earth's background and proper detection of such cosmic ray-produced charged particles such as muons and electrons can be implemented in a way that is especially sensitive to good shielding materials. A detection system can be configured to perform tomography of a target object under inspection based on scattering of muons and electrons by the target object. The system can be configured to perform tomography to localize scattering. The tomographic position resolution can be expressed approximately as follows:

$$\Delta x = \theta_{RMS} L$$

where:
$\theta_{RMS}$=the root-mean-square (rms) of the scattering angle, and
L=the size of the volume under the detection by the detection apparatus.
For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta \theta}{\theta} = \frac{1}{\sqrt{2N}}$$

where:
$\theta$=the rms scattering angle,
N=number of cosmic ray-produced muons and/or electrons passing through a region of interest. For example, the angular resolution for N=100 (corresponding to a 10×10 cm$^2$ resolution element after one minute of counting) is $\Delta\theta$=0.07$\theta$.

Tomographic methods, designed to construct an image or model of an object from multiple projections taken from different directions, can be implemented in the cosmic ray charged particle detection system to provide a discrete tomographic reconstruction of the volume of interest based on the data provided by the cosmic-ray charged particles entering and exiting the volume of interest. In some implementations, Monte Carlo simulation techniques can be used to study applications and shorten scanning times. Other stochastic processing methods may also be used in implementing the cosmic ray tomographic imaging described in this patent document.

Cosmic-Ray Based Charged Particle Detection System

The disclosed technology can utilize cosmic-ray background radiation for the interrogation of a VOI or region of interest (ROI), such as maritime cargo containers and other cargo conveyances for detection of target materials including nuclear and conventional weapons of mass destruction (WMD). FIG. 1 illustrates an exemplary detection system 100 for utilizing cosmic-ray charged particles to detect a target material in the VOI or ROI. The exemplary system 100 tracks muons and electrons generated in cosmic-ray interactions with the atmosphere before and after passing through a VOI or ROI. Measured multiple Coulomb scattering and attenuation interactions in the VOI or ROI are used to reconstruct the three-dimensional distribution of materials in the scanned volume. This distribution can reveal the presence of WMD, as well as components and precursors, without interfering with the flow of commerce.

The system 100 according to the disclosed technology utilizes charged particle detectors, such as large arrays of drift tubes, above and below the VOI. For example, system 100 includes a set of two or more planes or layers 110 of incoming position sensitive cosmic ray charged particle detectors 112 arranged above a volume 101 to be imaged for providing the position and angles (i.e., directions in the 3-D space) of incoming cosmic ray charged particle tracks 130 and 131. The incoming position sensitive cosmic ray charged particle detectors 112 can measure the position and angles of incoming cosmic ray charged particle tracks 130 and 131 with respect to two different directions, e.g., in two orthogonal coordinates along x and y axes. Cosmic ray charged particles (e.g., muons and electrons) pass through the volume 101 where the VOI 103 may be located and are scattered to an extent dependent upon the material occupying the volume 103 through which they pass. Another set of two or more planes or layers 120 of outgoing cosmic ray charged particle detectors 122 are positioned below the volume 101 and opposite to the planes or layers 110 of incoming cosmic ray charged particle detectors 112 to record outgoing or exiting cosmic ray charged particle positions and directions. The drift tubes in detectors 112 and 122 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks passing through the volume 101 in horizontal direction. The scattering angle of each charged particle is computed from the incoming and outgoing detector signal measurements.

In some implementations, each drift tube can be implemented using a simple metal (e.g., aluminum) tube with a thin wire strung down the center of the simple aluminum tube. Each tube is filled with a gas to provide controlled ionization and propagation (drift) of these ionized electrons to the wire and permanently sealed. In operation, a voltage is applied to the wire. Charged particles traversing the gas volume ionize the gas. Electrons from this ionization drift at a predictable rate toward the wire and avalanche near the wire to provide a pulse measurable at the end of the wire. In one example, the drift tubes can provide sub-millimeter position resolution perpendicular to the wire with widths of 5 cm and lengths up to 12 meters, providing geometric acceptance for very large scan volumes at relatively low cost. Tubes are placed in orthogonal layers to track charged particles in three-dimensions.

A signal processing unit 140, e.g., a computer, is provided in the system 100 to receive data of measured signals of the incoming cosmic ray charged particles by the position sensitive cosmic ray charged particle detectors 112 and outgoing cosmic ray charged particles by the position sensitive cosmic ray charged particle detectors 122. The signal processing unit 140 can analyze the scattering of the cosmic ray charged particles in the volume 101 based on the measured incoming and outgoing positions and directions of cosmic ray charged particles to obtain a tomographic profile or the spatial distribution of the scattering density reflecting the scattering strength or radiation length within the volume 101. The obtained tomographic profile or the spatial distribution of the scattering density within the volume 101 can reveal the contents of the VOI 103 in the volume 101. FIG. 1 shows drift tube detectors 112 and 122 are located on top (above the volume 101) and bottom (below the volume 101) of the volume 101. In some implementations, additional drift tube detectors can be implemented on sides positioned laterally or horizontally with respect to the volume 101 to form a box or four sided detection structure into which a package, a vehicle or cargo container can enter for scanning by the system.

The signal processing unit 140 of system 100 in FIG. 1 and other systems described in this application can process signals received from the position sensitive cosmic ray charged particle detectors associated with cosmic-ray charged particles traversing through a volume under inspection (e.g., a package, a container or a vehicle) to perform various operations. Incoming and outgoing particle trajectories are evaluated for multiple Coulomb scattering and attenuation caused by materials or objects in the volume of interest. These data are processed using imaging techniques to reconstruct the 3D material distribution in the VOI. This distribution is then automatically evaluated to determine the presence of defined threats.

For example, the signal processing unit 140 can process the signals received from the position sensitive cosmic ray charged particle detectors to reconstruct the trajectory of a cosmic ray charged particle such as a muon or an electron traversing through the volume 101. The signal processing unit 140 can measure the momentum of an incoming cosmic ray charged particle based on signals received from the position sensitive cosmic ray charged particle detectors 112. The signal processing unit 140 can measure the momentum of an outgoing cosmic ray charged particle based on signals received from the position sensitive cosmic ray charged particle detectors 122. The signal processing unit 140 can determine the spatial distribution of the scattering density of the volume 101. Results from the signal processing unit 140 processing the signals received from the position sensitive cosmic ray charged particles can be used to construct the tomographic profile and measure various properties of the volume 101.

Also, the process for reconstructing the trajectory of a cosmic ray charged particle traversing or passing through a cosmic ray charged particle detector having a set of drift cells can include obtaining hit signals representing identifiers of drift cells hit by cosmic ray charged particles and corresponding hit times. The cosmic ray charged particle trajectory reconstruction process can include grouping in-time drift cell hits identified as being associated with a track of a particular cosmic ray charged particle passing through the corresponding position sensitive cosmic ray charged particle detector. The cosmic ray charged particle trajectory reconstruction process can include initially estimating a time zero value for a moment of time at which the particular cosmic ray charged particle hits a given drift cell. The cosmic ray charged particle trajectory reconstruction process can include determining drift radii based on estimates of the time zero values, drift time conversion data and the time of the hit. The cosmic ray charged particle trajectory reconstruction process can include fitting linear tracks to drift radii corresponding to a particular time zero value. Also, the cosmic ray charged particle trajectory reconstruction process can include searching and selecting a time-zero value associated with a perceived near best or ideal of the track fits performed for a particular charged particle and computing error in time-zero and tracking parameter. Reconstruction of the track based on the time zero fit provides a reconstructed linear trajectory of the cosmic ray charged particle passing through the position sensitive cosmic ray charged particle detector without having to use fast detectors (such as photomultiplier tubes with scintillator paddles) or some other fast detector which detects the passage of the muon through the apparatus to the nearest few nanoseconds to provide the time-zero.

Also, the processing for measuring the momentum of an incoming or outgoing cosmic ray charged particle based on signals from the position sensitive cosmic ray charged particle detectors (i.e., detector signals) can include, for example, configuring position sensitive cosmic ray charged particle detectors to scatter a cosmic ray charged particle passing through the position sensitive cosmic ray charged particle detectors. The process for measuring the momentum of an incoming or outgoing cosmic ray charged particle based on detector signals include measuring the scattering of a charged particle in the position sensitive detectors. Measuring the scattering can include obtaining at least three positional measurements of the scattering cosmic ray charged particle. The process for measuring the momentum of an incoming or outgoing cosmic ray charged particle based on detector signals include determining at least one trajectory of the cosmic ray charged particle from the positional measurements. The process for measuring the momentum of an incoming or outgoing cosmic ray charged particle based on detector signals include determining at least one momentum measurement of the charged particle from the at least one trajectory. This technique can be used to determine the momentum of the cosmic ray charged particle based on the trajectory of the cosmic ray charged particle. The trajectory of the cosmic ray charged particle is determined from the scattering of the cosmic ray charged particles at the position sensitive cosmic ray charged particle detectors themselves without the use of additional metal plates in the detector.

Also, the spatial distribution of the scattering density of the volume can be determined from cosmic ray charged particle tomographic data by obtaining predetermined cosmic ray charged particle tomography data corresponding to scattering angles and estimated momentum of cosmic ray charged particles passing through object volume. Determining the spatial distribution of the scattering density of the volume from cosmic ray charged particle tomographic data can include providing the probability distribution of charged particle scattering for use in an image reconstruction technique such as an expectation maximization (ML/EM) technique, the probability distribution being based on a statistical multiple scattering model. Also, determining the spatial distribution of the scattering density of the volume from cosmic ray charged particle tomographic data can include determining an estimate of the object volume density, e.g., by determining a substantially maximum likelihood estimate using the expectation maximization (ML/EM) technique. Determining the spatial distribution of the scattering density of the volume from cosmic ray charged particle tomographic data can include outputting reconstructed object volume scattering density. The reconstructed object volume scattering density can be used to identify the presence and/or type of object occupying the volume of interest from the reconstructed volume density profile. Various applications include cosmic-ray charged particle tomography for various homeland security inspection applications in which vehicles or cargo can be scanned by a charged particle tracker.

The tomographic processing part of the signal processing unit 140 may be implemented in a computer at the same location as the detectors 112 and 122. Alternatively, the tomographic processing part of the signal processing unit 140 may be implemented in a remote computer that is connected on a computer network such as a private network or a public network such as the Internet.

In FIG. 1, incoming cosmic ray charged particle detectors 112 can detect the X-Y position, angle, speed, and momentum of each of the incident cosmic ray charged particles 130 and 131 entering the volume 101, while outgoing cosmic ray charged particle detectors 122 can detect the X-Y position, angle, speed, and momentum of each of the exiting charged particles 130 passing through volume 101. The signal processing unit 140 can process the position, angle, speed, and momentum data collected by position sensitive cosmic ray charged particle detectors 112 and 122 to match each incident charged particle 130 with a corresponding exiting cosmic ray charged particle 130. Also, the signal processing unit 140 can process the position, angle, speed, and momentum data collected by position sensitive cosmic ray charged particle detectors 112 and 122 to identify those exiting cosmic ray charged particles 130 that are scattered by VOI 103, such as cosmic ray charged particles 130', and generate a scattering number for the incident cosmic ray charged particles. The signal processing unit 140 can process the position, angle, speed, and momentum data collected by position sensitive cosmic ray charged particle detectors 112 and 122 to identify incident cosmic ray charged particles 131 stopped inside VOI 103 and generate a stopping number for the incident cosmic ray charged particles.

Further detail of cosmic-ray particle tomography systems which can be used to detect and identify content of a VOI exposed to cosmic-ray particles based on the measured scattering and stopping characteristics of the cosmic-ray particles is described in U.S. Pat. No. 8,247,767 entitled "PARTICLE DETECTION AND APPLICATIONS IN SECURITY AND PORTAL MONITORING" filed on Oct. 26, 2007, the content of which is incorporated by reference as part of the specification of this application.

Figure 2A:
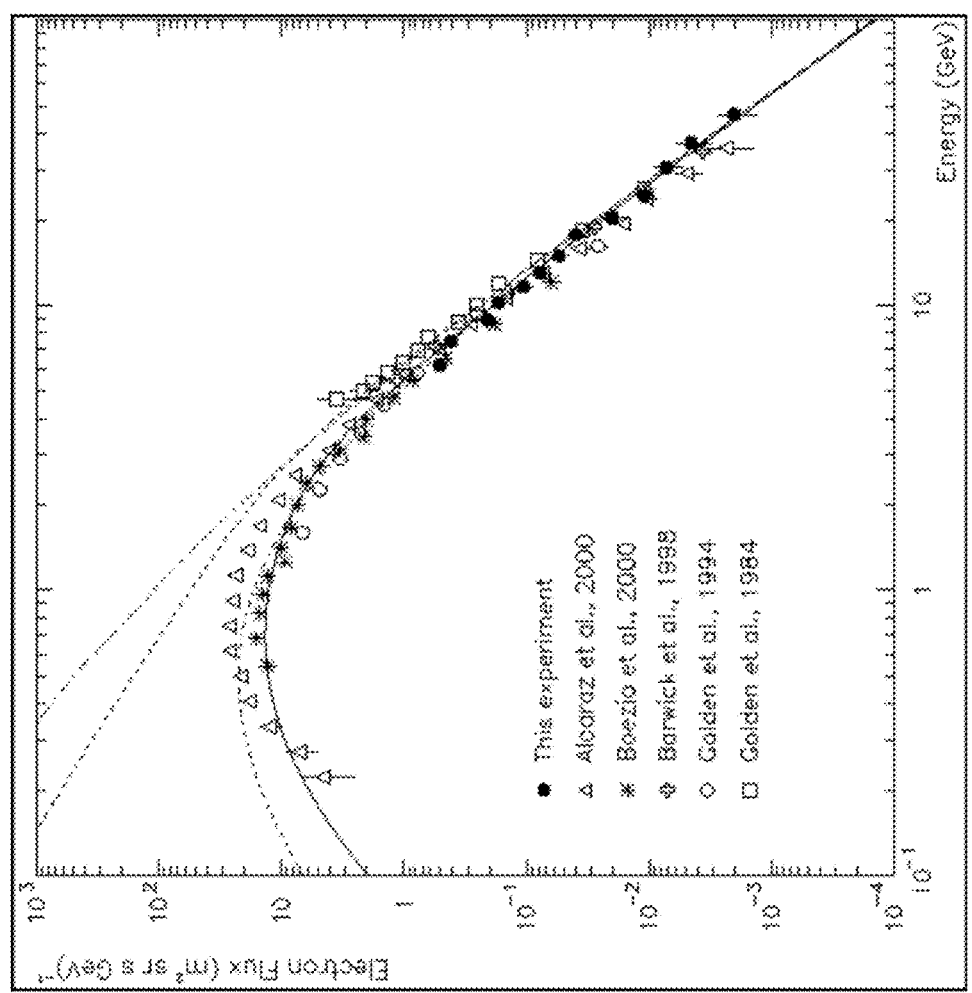
FIG. 2A shows a data plot of cosmic ray electron energy spectrum at sea level.
Figure 2B:
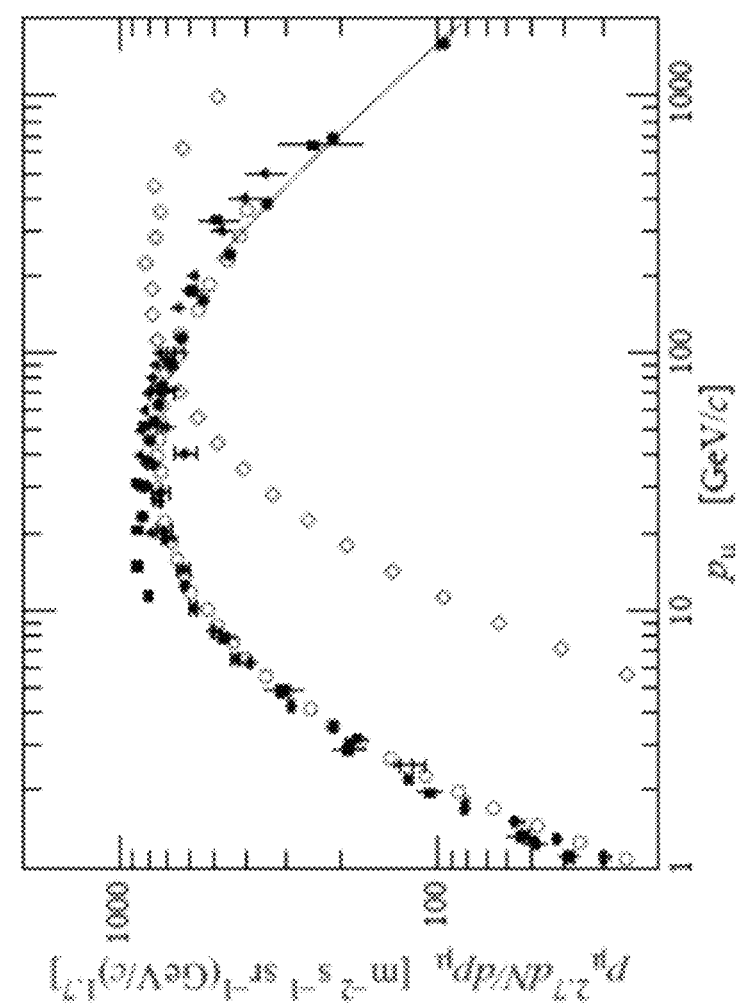
FIG. 2B shows a data plot of cosmic-ray muon momentum spectra for vertical)(0° and low-incident-angle)(75° muons.

The majority of cosmic-ray charged particles reaching the Earth's surface are electrons and muons produced as showers of secondary products of the interaction between more massive particles and the upper atmosphere. These two species of cosmic ray charged particles occupy substantially different parts of the energy spectrum, while some overlap can exist. FIG. 2A shows a data plot of cosmic ray electron energy spectrum at sea level (from C. Grimani et al., "Measurements of the absolute energy spectra of cosmic-ray positrons and electrons above 7 GeV", Astron. Astrophys. 392, 287-294, 2002). As shown in FIG. 2A, most electrons have energies between about 0.3 and 1 GeV (i.e., giga electron volts). FIG. 2B shows a data plot of cosmic-ray muon momentum spectra for vertical)(0° and low-incident-angle)(75° muons (from J. Beringer, "Cosmic Rays", Particle Data Group, Lawrence Berkeley Lab, 2012, accessed at pdg.lbl.gov/2012/reviews/rpp2012-rev-cosmic-rays.pdf).

As can be seen in FIG. 2B, most muons have energies between about 0.5 and 200 GeV. Also can be observed from these plots that electrons have a mean energy of about 0.7 GeV, and muons have a mean energy of about 3.7 GeV. The overlap in the electron and muon spectra represents a small fraction of the total flux.

Multi-Mode Passive Detection System (MMPDS) & Detection Process

Because the detection and/or imaging techniques performed by the disclosed muon and electron detection systems are entirely passive, e.g., relying on natural, ambient cosmic rays and on natural emission of gamma rays and/or induced emission of neutrons from materials of the target object, the disclosed detection system can also be referred to as a Multi-Mode Passive Detection System (MMPDS). The drift tubes of the MMPDS can be used to sense cosmic-ray electrons. More specifically, the drift tubes of the MMPDS which are used to sense cosmic-ray muons can be used here to sense cosmic-ray electrons.

The disclosed technology includes a method to apply cosmic-ray tomography in a manner that can detect and characterize not only dense assemblages of heavy nuclei (like Special Nuclear Materials, SNM) but also assemblages of medium- and light-atomic-mass materials (such as metal parts, conventional explosives, and organic materials). Characterization may enable discrimination between permitted content in commerce and contraband (explosives, illegal drugs, and the like). The disclosed MMPDS can rely primarily on the muon component of cosmic rays to interrogate VOI. Muons, highly energetic, pass essentially un-scattered through materials of light atomic mass and are only weakly scattered by conventional metals used in industry. Substantial scattering and absorption only occur when muons encounter sufficient thicknesses of heavy elements characteristic of lead and SNM. Since electrons are appreciably scattered by light elements and stopped by sufficient thicknesses of materials containing medium-atomic-mass elements (metals, etc.), combining the response of muons and electrons can extend the range of material detection and characterization beyond SNM to other types of contraband.

An MMPDS as disclosed in this patent document can measure both scattering signals and stopping signals of muons and electrons passing through a VOI. In some implementations, to establish a relationship of scattering to stopping of cosmic ray charged particles over a range of low-density materials, a given material within a range of low-density materials is characterized to obtain a scattering parameter and a stopping parameter. A given material being characterized may be placed inside a container, which creates a measurement environment to mimic an actual environment of cosmic-ray imaging and detection. For example, the container can be a shipping container, a cargo container, a compartment of a vehicle (such as the truck of the vehicle), or a package. In some embodiments, an empty container may be measured separately to establish the background measurement. The same container may be used to enclose the VOI for different materials. The scattering-stopping relationship for a range of low-density materials can be established based on the determined pairs of scattering and stopping parameters.

For a given material being measurement, the MMPDS can be used to determine the scattering and stopping of cosmic ray charged particles (including cosmic-ray electrons and cosmic-ray muons) when the VOI is exposed to the cosmic-ray charged particles. In some embodiments, determining the scattering of cosmic ray charged particles includes using a first set of position sensitive cosmic ray charged particle detectors of the MMPDS located above the VOI to detect events of incident cosmic ray charged particles that penetrate the first set of position sensitive cosmic ray charged particle detectors to enter the VOI, and using a second set of position sensitive cosmic ray charged particle detectors of the MMPDS located below the VOI and opposite to the first set of position sensitive cosmic ray charged particle detectors to detect events of outgoing cosmic ray charged particles exiting the VOI. A signal processing unit of MMPDS can be used to receive signals of the incident cosmic ray charged particles from the first set of position sensitive cosmic ray charged particle detectors and signals of the outgoing cosmic ray charged particles from the second set of position sensitive cosmic ray charged particle detectors. The signal processing unit can determine a scattering parameter of the cosmic ray charged particles based on the received signals of the incoming cosmic ray charged particles and the outgoing cosmic ray charged particles. For example, the received signals of the incident cosmic ray charged particles from the first set of position sensitive cosmic ray charged particle detectors can be used to determine a number of incident cosmic ray charged particles and the received signals of the outgoing cosmic ray charged particles from the second set of position sensitive cosmic ray charged particle detectors can be used to determine a number of scattered cosmic ray charged particles. The difference between the number of incident cosmic ray charged particles and scattered cosmic ray charged particles can be used as a measurement of the stopped cosmic ray charged particles. This difference may be referred to as "the raw stopping number."

One aspect of the disclosed technology provides a technique for determining a charged particle stopping parameter for an object associated with a VOI. The technique takes into account effects of the object geometry and placement within the MMPDS. The raw stopping number can be affected by the object placement within the MMPDS. An increased number of scattered (i.e., unstopped) tracks can exit the object without passing through the position sensitive cosmic ray charged particle detectors when the object is located near the edges of the MMPDS. Hence, the raw stopping number as described above may tend to overestimate the stopping in such object placements because fewer scattered tracks are detected. To mitigate this problem, a stopping parameter of a sample, referred to as "stopping power," is developed to mitigate the effects of the sample geometry and placement location within the MMPDS.

A stopping power can be obtained by adjusting the raw stopping number to adequately account for the undetected scattered tracks. In one implementation, the stopping power of an object can be obtained by dividing the raw measurement of the number of stopped tracks (or the "raw number of stopped tracks") by the number of scattered tracks that are detected. The raw number of stopped tracks can be computed as the number of incident tracks detected minus the number of scattered tracks detected. Because not all scattered tracks are detected equally efficiently in all parts of the MMPDS (particularly near the edges of the detector arrays of the MMPDS), dividing the raw number of stopped tracks by the number of scattered tracks normalizes for variations in detection efficiency at different locations of the MMPDS. For example, when an object is placed near the center of the MMPDS, the corresponding raw number of stopped tracks tends to be bigger but it is adjusted through the stopping power parameter by a bigger number of scattered tracks. On the other hand, when an object is placed near an edge of the MMPDS, the corresponding raw number of stopped tracks may be smaller but it is adjusted through the stopping power parameter by a smaller number of scattered tracks.

Stopping Power Model

In some implementations, the stopping power of an object is expressed as follows:

$$\text{Stopping Power} = \frac{(\text{raw number of stopped tracks/area/time}) \times \langle p \rangle}{(\text{number of scattered tracks/area/time}) \times \text{sample property}}, \quad (1)$$

where $\langle p \rangle$ is the average momentum of the incident cosmic rays, and the raw number of stopped tracks is obtained as the number of incident tracks detected minus the number of scattered tracks detected. The stopping power computation of Eqn (1) not only takes into account the above-described object placement effects, it is also normalized for effects of the sample property. For example, the sample property in Eqn (1) can be the sample thickness. Sample thickness can be a known value or estimated using other means (such as obtained from a reconstruction image). The above-described stopping power computation is used to obtain the stopping parameter shown in FIGS. 3 and 4 below, which also use samples of known thickness. In some implementations, the sample stopping power computations of Eqn (1) is normalized for the effects of the sample property that includes the average path length through the material in the sample. Using the average path length tracked by the detection system, the stopping power computing of Eqn (1) can be accurately obtained.

Figure 3:
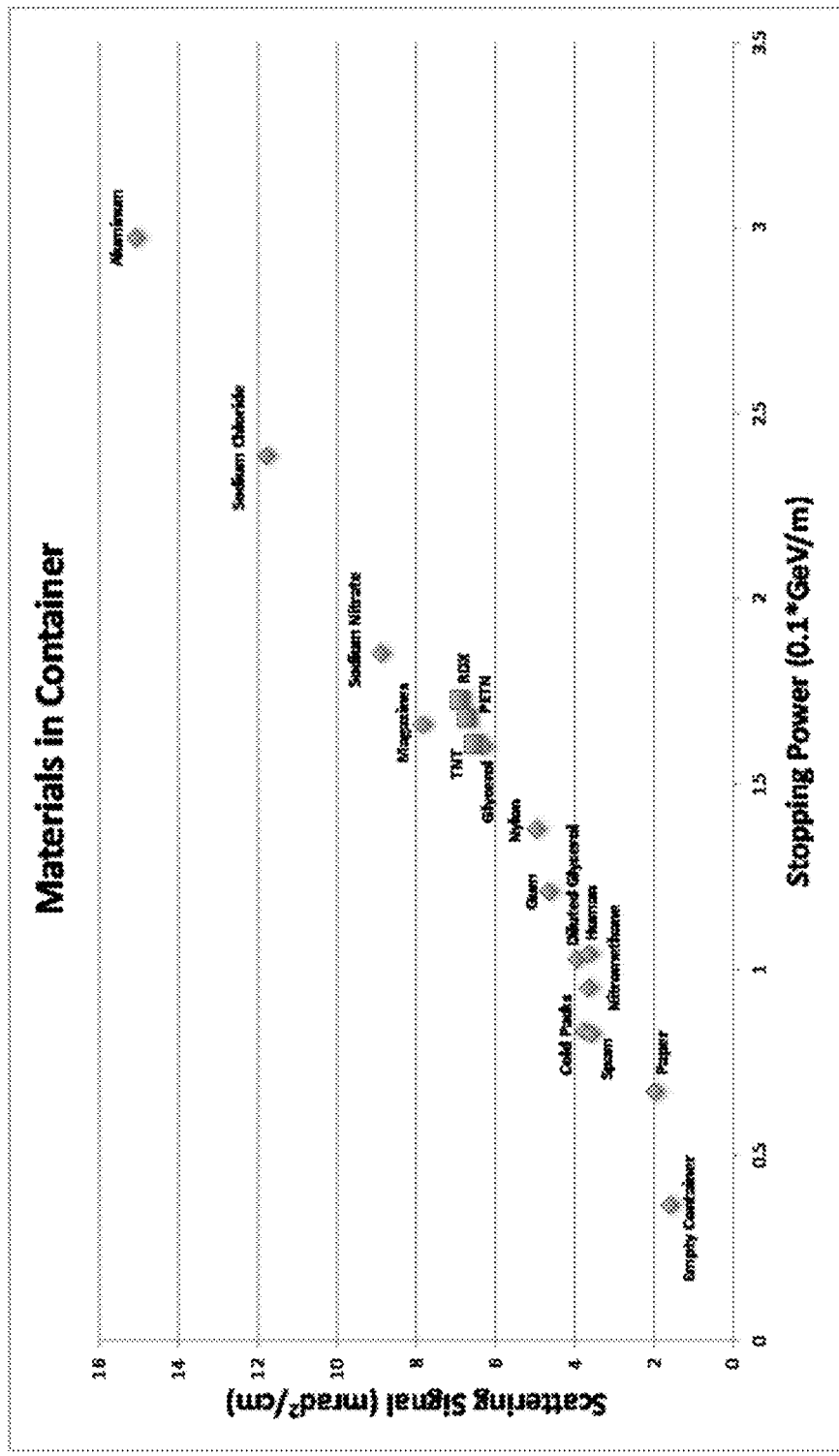
FIG. 3 shows measured data plot for a wide range of materials (in blue) placed inside a shipping container where scattering of cosmic-ray particles is plotted against stopping of cosmic-ray particles in accordance with some embodiments described herein.

FIG. 3 shows measured data plot for a wide range of materials (in blue diamond shapes) placed inside an shipping container where scattering of cosmic-ray particles is plotted against stopping of cosmic-ray particles in accordance with some embodiments described herein. As can be seen in FIG. 3, the range of materials extends from air (i.e., an empty container) to aluminum. Red symbols (square shapes) near the middle of the data plot show the modeled, predicted locus of conventional high explosives TNT, RDX and PETN. In the example shown, data are measured inside a shipping container, and therefore all data points in the plot include the effect of the container's metal walls. The empty container provides the data point closest to the origin. Because the container's walls are constructed with relatively thin metal sheets, the volume is mostly air. Also, the data plot shows a clear monotonic relationship between scattering and stopping of cosmic-ray particles over the range of low-density materials. The monotonic relationship is approximately linear. Both the scattering and stopping of cosmic-ray particles appear to be monotonically increasing with the atom-mass of the materials. In some embodiments, the stopping signal of cosmic ray charged particles is obtained using a raw number of stopped cosmic ray charged particles adjusted for the effects of the sample placement location relative to the detector based on Eqn (1).

Figure 4:
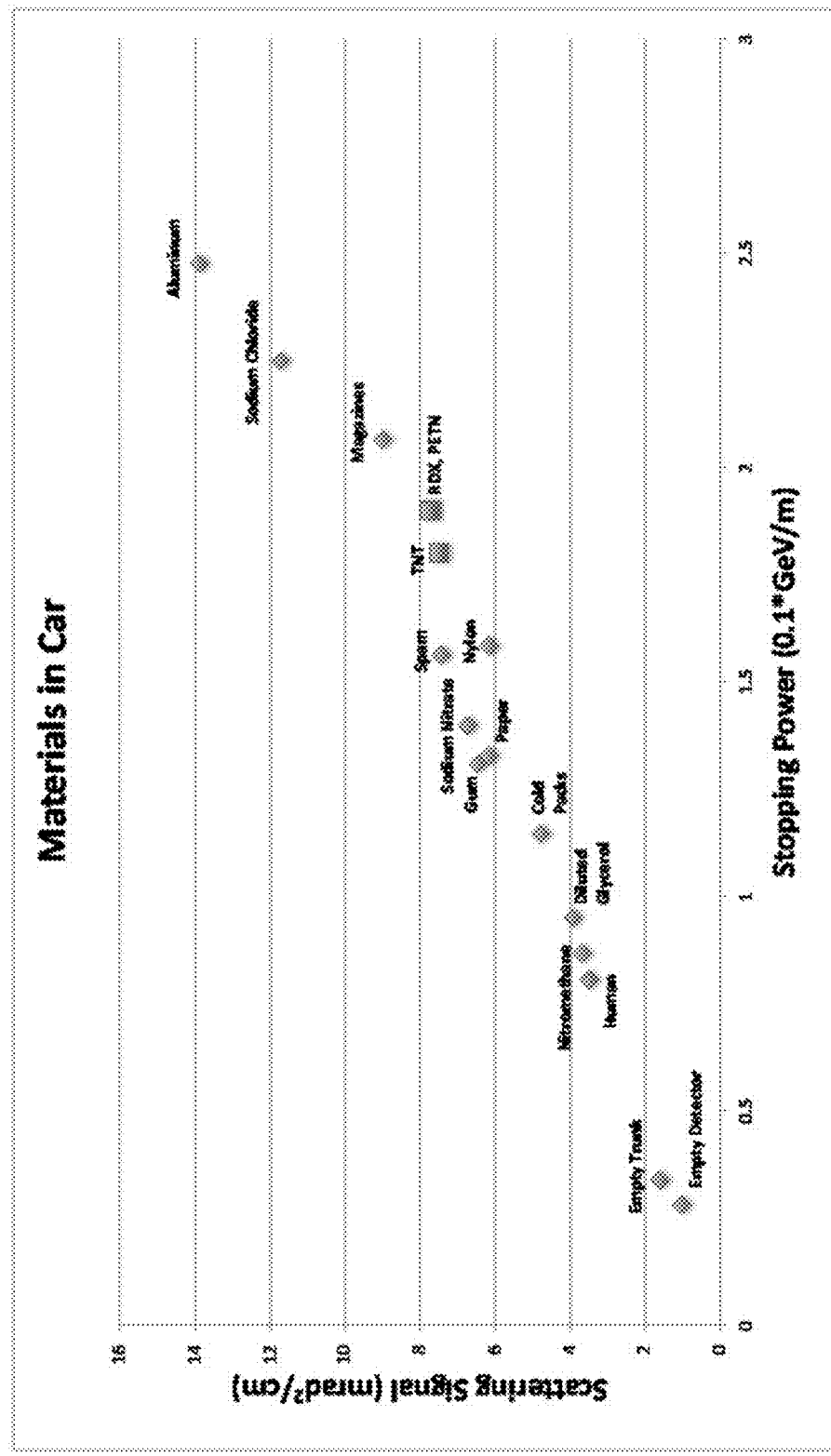
FIG. 4 shows measured data plot for a wide range of materials (in blue) placed inside the trunk of an automobile where scattering of cosmic-ray particles is plotted against stopping of cosmic-ray particles in accordance with some embodiments described herein.

FIG. 4 shows measured data plot for a wide range of materials (in blue diamond shapes) placed inside the trunk of an automobile where scattering of cosmic-ray charged particles is plotted against stopping of cosmic-ray charged particles. On the bottom left we see the lowest points for an empty detector and empty trunk which give a measure of the background signals due to the scattering and stopping in the detector elements and the car trunk area. The materials are spread out mostly towards the top right. The red squares are from simulations of explosives that were placed where they are predicted to lie. As FIG. 4 shows, the effect of the container becomes more pronounced because it encloses a smaller volume. The relationship appears to acquire a bit of nonlinearity, possibly as a consequence of the increased metal content of the car, relative to the contents inside the trunk. However, the overall relationship remains monotonic and approximately linear.

Figure 5:
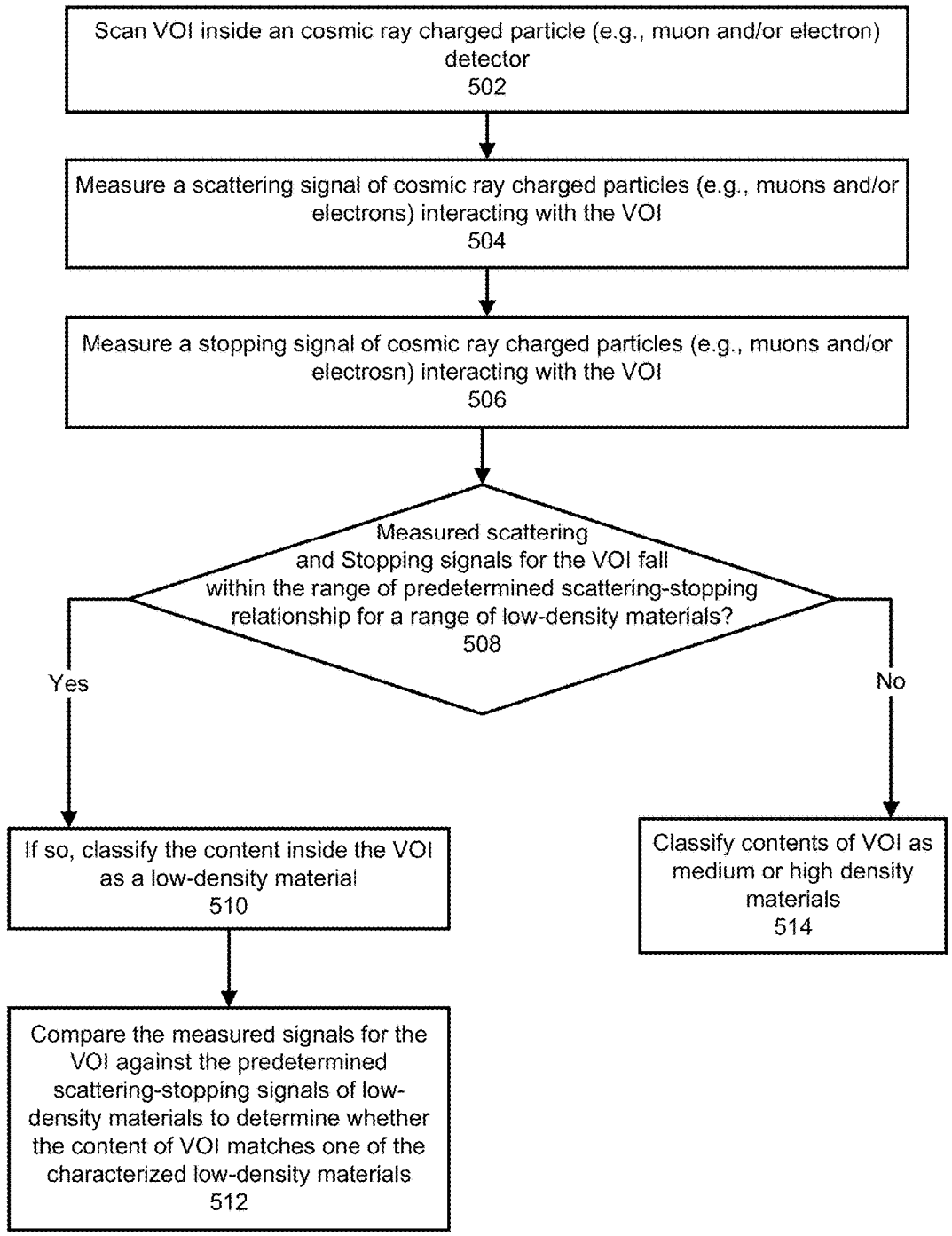
FIG. 5 presents a flowchart illustrating a process for identifying the content inside a VOI using cosmic-ray particles in accordance with some embodiments described herein.

Once the scattering-stopping relationship has been measured for the range of low-density materials, the measured relationship can be used to detect and identify the contents within a VOI exposed to charged particles. FIG. 5 presents a flowchart illustrating an exemplary process for identifying contents inside an VOI using cosmic-ray charged particles.

The process can include scanning a VOI positioned inside a cosmic ray charged particle detector, such as a MMPDS (502). The process includes measuring a scattering signal of cosmic-ray charged particles interacting with the VOI (504). Also, the process includes measuring a stopping signal of cosmic-ray particles interacting with the VOI (506).

For example, a MMPDS may be used to measure the scattering and stopping signals in terms of the numbers of scattered and stopped cosmic ray charged particles (including cosmic-ray electrons and cosmic-ray muons). The MMPDS may include a first set of position sensitive cosmic ray charged particle detectors of the MMPDS located above the VOI to detect events of incident cosmic ray charged particles that penetrate the first set of position sensitive cosmic ray charged particle detectors and enter the VOI. The MMPDS can include a second set of position sensitive cosmic ray charged particle detectors located below the VOI and opposite to the first set of position sensitive cosmic ray charged particle detectors to detect events of outgoing cosmic ray charged particles exiting the VOI. A signal processing unit of MMPDS can receive signals of the incident cosmic ray charged particles from the first set of position sensitive cosmic ray charged particle detectors and signals of the outgoing cosmic ray charged particles from the second set of position sensitive cosmic ray charged particle detectors. The signal processing unit can determine the number of scattered cosmic ray charged particles per area per unit time based on the received signals of the outgoing cosmic ray charged particles, and can determine a raw number of stopped cosmic ray charged particles per area per unit time based on the number of scattered cosmic ray charged particles from the number of incident cosmic ray charged particles. In some embodiments, the raw number of stopped cosmic ray charged particles can be adjusted for the effect of the VOI location relative to the position sensitive cosmic ray charged particle detector based on Eqn (1).

The process can include determining whether the measured scattering and stopping signals for the VOI fall within the range of predetermined scattering-stopping relationship for a range of low-density materials (508). When determined that the measured scattering and stopping signals for the VOI fall within the range of predetermined scattering-stopping relationship for a range of low-density materials, the contents inside the VOI can be classified as a low-density material (510) and the pair of scattering and stopping signals for the VOI can be compared against the predetermined scattering-stopping signals of low-density materials to determine whether the contents of the VOI matches one of the characterized low-density materials (512). The measured stopping signal can be used to infer or estimate the thickness of the contents. In some implementations, an average path length through the material can be determined to normalize the comparison of the stopping and scattering signals. When the measured scattering and stopping signals fall outside of range of predetermined scattering-stopping relationship, the contents of the VOI may be classified as medium or high density materials (514).

The material identification process can include a compensating or mitigating process for the geometric effects of the object being detected to improve the accuracy of the detection. For objects shaped like horizontal planes (e.g., sheets, slabs), substantially all of the cosmic ray produced charged particles traverse the same thickness (or are stopped by the same thickness) as they penetrate the object. However, objects whose horizontal extent is comparable to or smaller than their vertical thickness can have a substantial number of cosmic ray charged particles with trajectories cutting through corners, and the path lengths of such cosmic ray charged particles can be much shorter than the path lengths of cosmic ray charged particles penetrating the entire thickness of the objects. This effect can skew the observed scattering and stopping power. This skewing, however, can be mitigated by repeating the data reduction, selecting different-sized subsets (i.e., masks) of the VOI for analysis. A mask much smaller than the full horizontal extend of an object will include a smaller fraction of cosmic ray charged particle trajectories cutting the corners, and thus have smaller systematic error. Varying the mask size can quantify the error, as well as yielding better estimates of both thickness and horizontal dimensions.

Because muons can be used to detect a wide range of medium or high-atomic-mass materials, a relationship between scattering and stopping of muons can be constructed over a wide range of medium to high-atomic-mass materials using substantially the same disclosed techniques for constructing the scattering and stopping relationship for the range of low-atomic-mass materials using cosmic-ray charged particles. When computing a corresponding stopping parameter for the muons based on the raw number of stopped muons, the same technique for correcting the raw number of stopped charged particles can be used to correct the raw number of stopped muons to compensate for effects of the placement location of the VOI inside the muon detector. The characterized relationship between scattering and stopping of muons for the range of medium and high-atomic-mass materials can be combined with the characterized relationship between scattering and stopping of charged particles for the range of low-atomic-mass materials to extend the range of material detection and characterization to an even greater range of materials beyond SNM to other types of contraband.

Moreover, the disclosed MMPDS does not apply radiation to the scene being scanned. This means scanning can be performed concurrently with existing operations without endangering workers, operators or drivers. Scan results are delivered in real-time with no human interpretation required, reducing impact on commerce flow and operational costs. Another advantage of this technology is the ability to acquire additional information with extended scanning Typical scan times are on the order of minutes for clearing of benign cargo. For suspicious configurations, more detail can be obtained by extending the scan time, providing for the clearance of benign cargo or enhanced information for responders in the event of threat detection.

The ratio of stopping power to scattering, where the latter is given by the expression $\lambda = (<\theta><p>)^2/[\text{sample thickness}]$ and $<\theta>$ is the average sample scattering angle, enables one to eliminate sample thickness as an unknown (since stopping power is also normalized by sample thickness, so the ratio eliminates that variable). The ratio enables material identification, and then the mean scattering angle can be used to infer the sample thickness. In some implementations, rather than using the sample thickness in the expression $\lambda = (<\theta><p>)^2/[\text{sample thickness}]$, an average path length through the material can be used.

Figure 6:
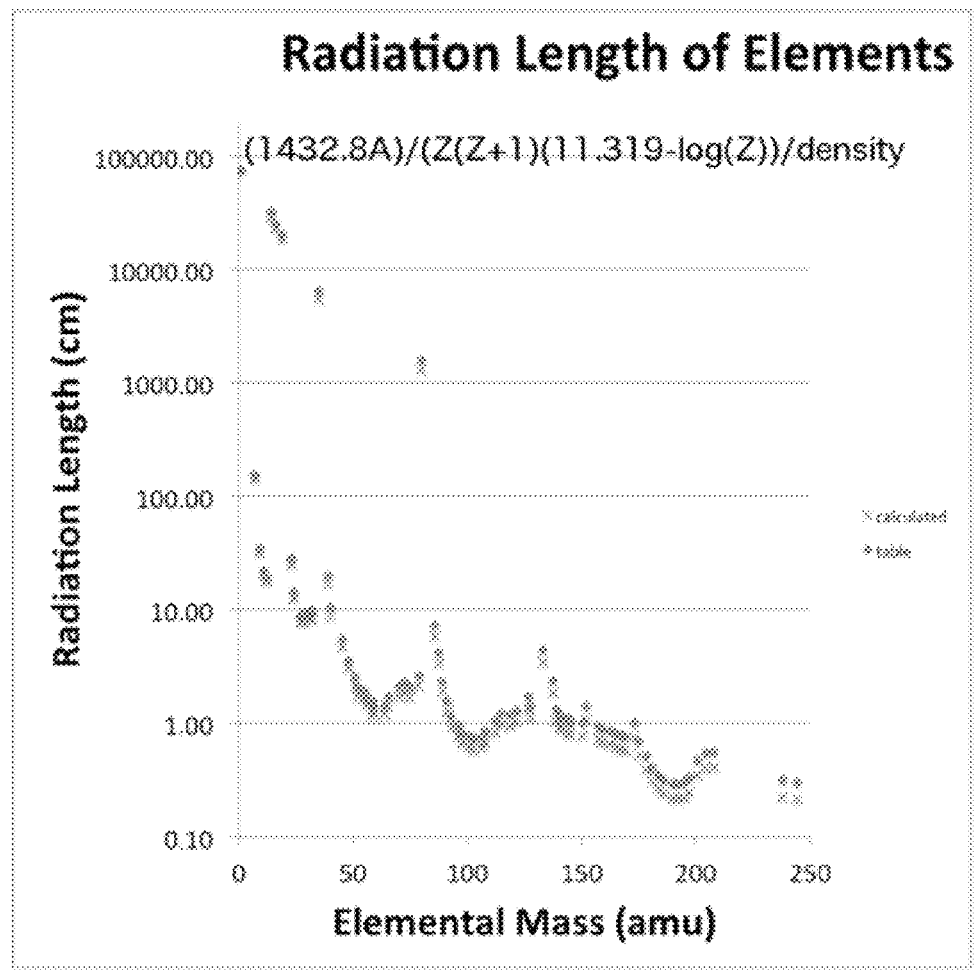
FIG. 6 shows exemplary radiation length of most of the elements both measured and fit with the formula.

An expression used to connect the scattering to the number of radiation lengths of a material can be described as follows. If one assumes the average momentum is 3 GeV, then $\lambda = 21.47/R$ (cm) where R is the radiation length of the material. The radiation lengths of most of the elements is given in FIG. 6. FIG. 6 shows the radiation length of most of the elements both measured and fit with the formula.

For matter such as water we can use the elemental data to compute the radiation length using the formula and bulk density $R(H2O)=3/\{[2/(R(H)*\rho(H))]+[1/(R(O)*\rho(O)]\}/\rho(H2O)$.

Figure 7:
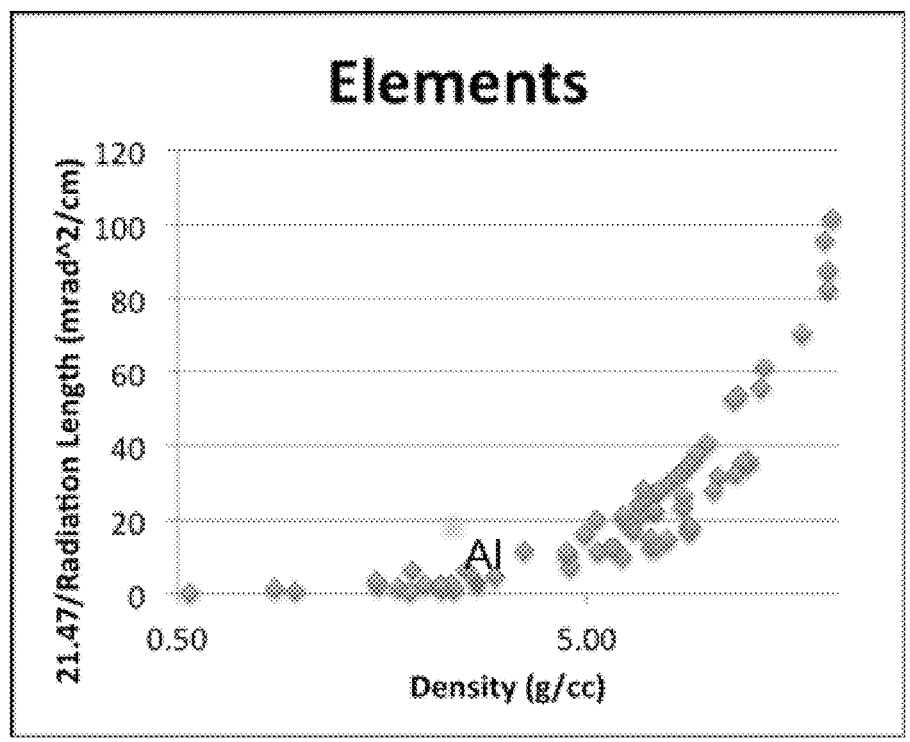
FIG. 7 shows predicted scattering plotted as a function of density for the elements.

The actual stopping (per thickness or per average path length through the material) depends on dE/dx, the tracking of electrons through the detector, and the density of the material. The electrons and muons are all near the minimum ionizing region. The density can be used as an indication of the stopping, and the expression for connect the scattering to the number of radiation lengths of a material for the scattering. FIG. 7 shows predicted scattering plotted as a function of density for the elements. The position of metallic aluminum is marked in the figure. Elements to the left of aluminum have a large variation in density while to the right it is the scattering that is changing more rapidly.

Figure 8:
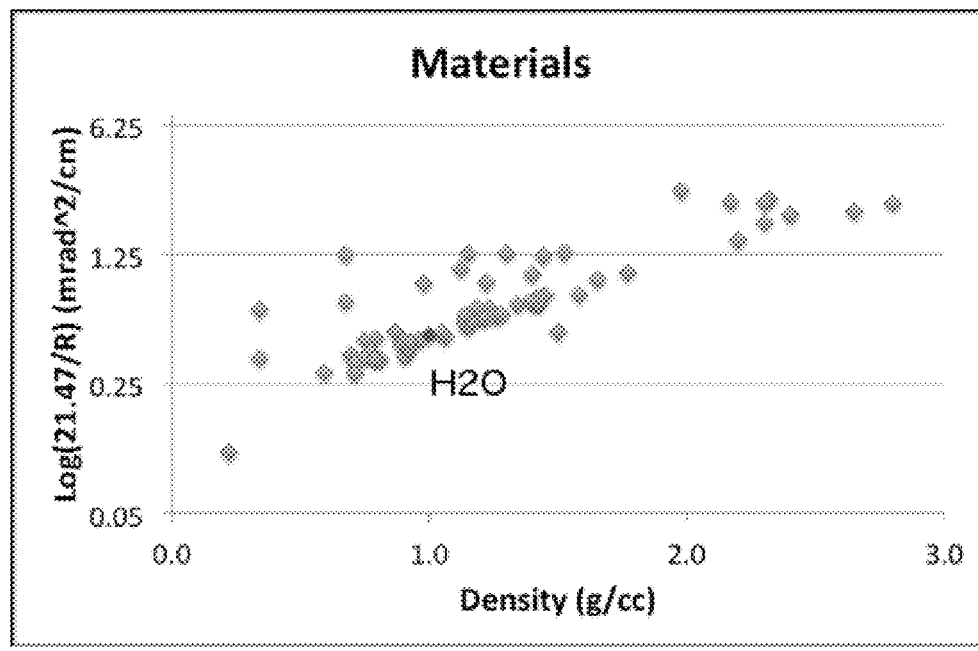
FIG. 8 shows an exemplary predicted scattering as a function of density for materials.

FIG. 8 shows an exemplary predicted scattering as a function of density for materials. Most commonly found materials in commerce are in the low density region below 3 g/cc. The value for water is marked for reference.

Figure 9:
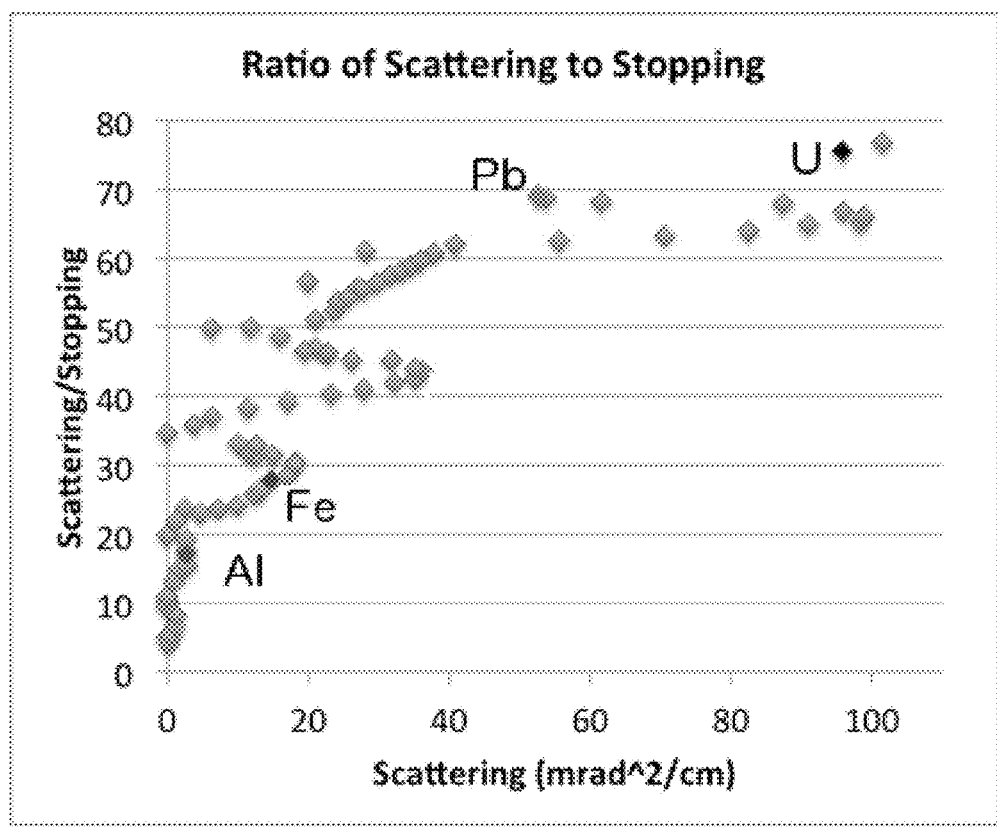
FIG. 9 shows an exemplary ratio of the predicted scattering divided by the density as a function of scattering for the elements.

FIG. 9 shows an exemplary ratio of the predicted scattering divided by the density as a function of scattering for the elements. FIG. 9 shows that the ratio of scattering to density is able to separate the different regions of density and can clearly separate the four metals shown, aluminum, iron, lead and uranium. The differences in radiation lengths due to the atomic shell effects that are seen in FIG. 6 result in the horizontal structure that is seen in FIG. 9.

Simulated Results

In the simulation and experimental data we extract the stopping-to-scattering and ratio as stopping signal={number stopped crossing a rectangular volume/time}/(number scattered tracks crossing a rectangular volume/time)/thickness. In some implementations, rather than using the thickness estimation, an average path length through the material can be used.

Figure 10:
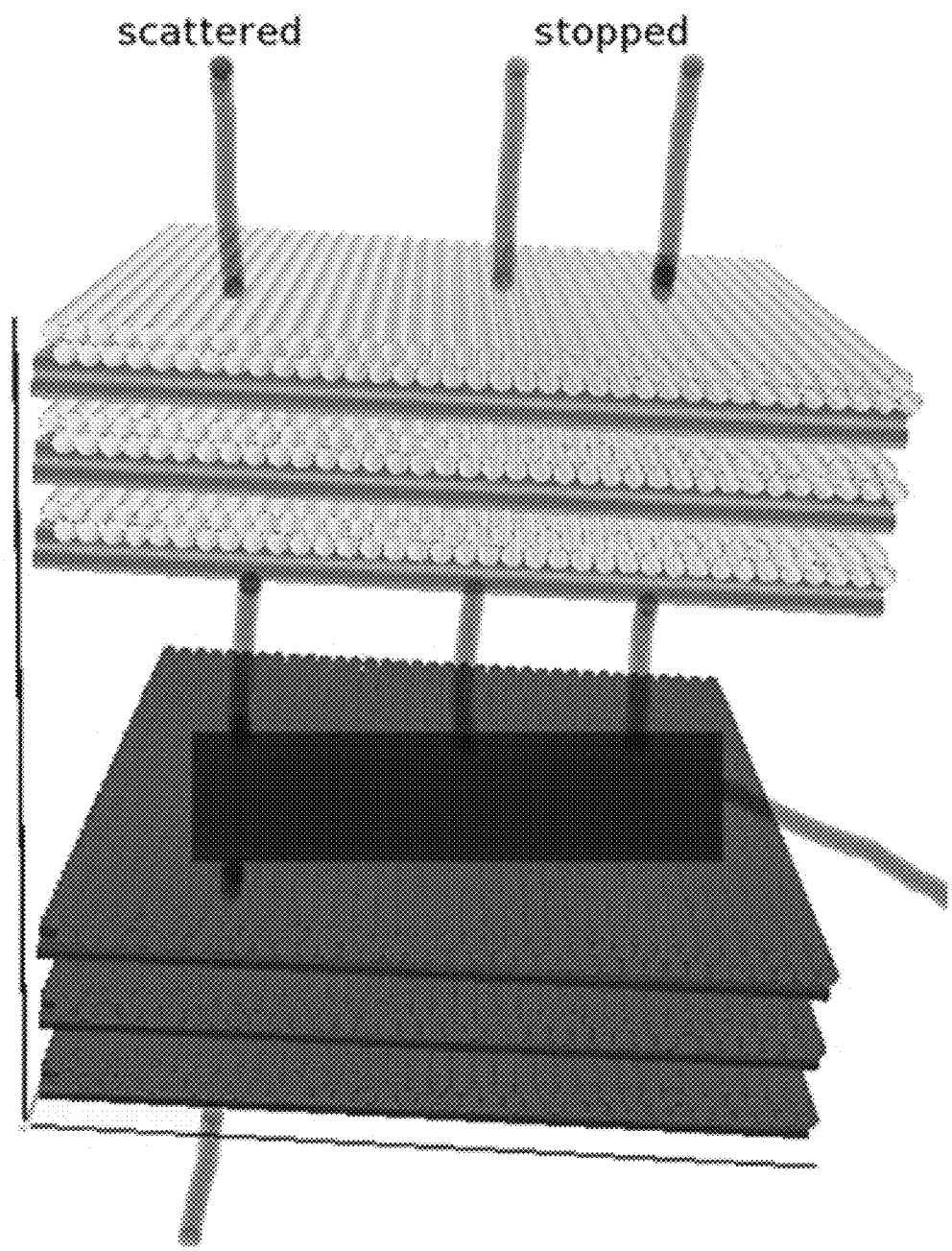
FIG. 10 shows three examples of incident muons or electrons.

Variations due to acceptance of detector and altitude of measurements are not accounted for in the data presented. FIG. 10 shows three examples of incident muons or electrons. The one on the left is a scattered particle that went through the blue sample. The middle particle stops before it reaches the bottom detector. The one on the right scatters at a very large angle from the blue sample and also does not reach the bottom detector. It is also counted as a stopped particle in both the data and simulation. While one cannot know whether any particular charged particle is a muon or an electron, their momentum spectra are quite different so that in the same material the electrons tend to scatter and stop more than muons. The muons dominate the scattering signal because there are more of them at energies sufficient for good tracking through the detector.

Figure 11:
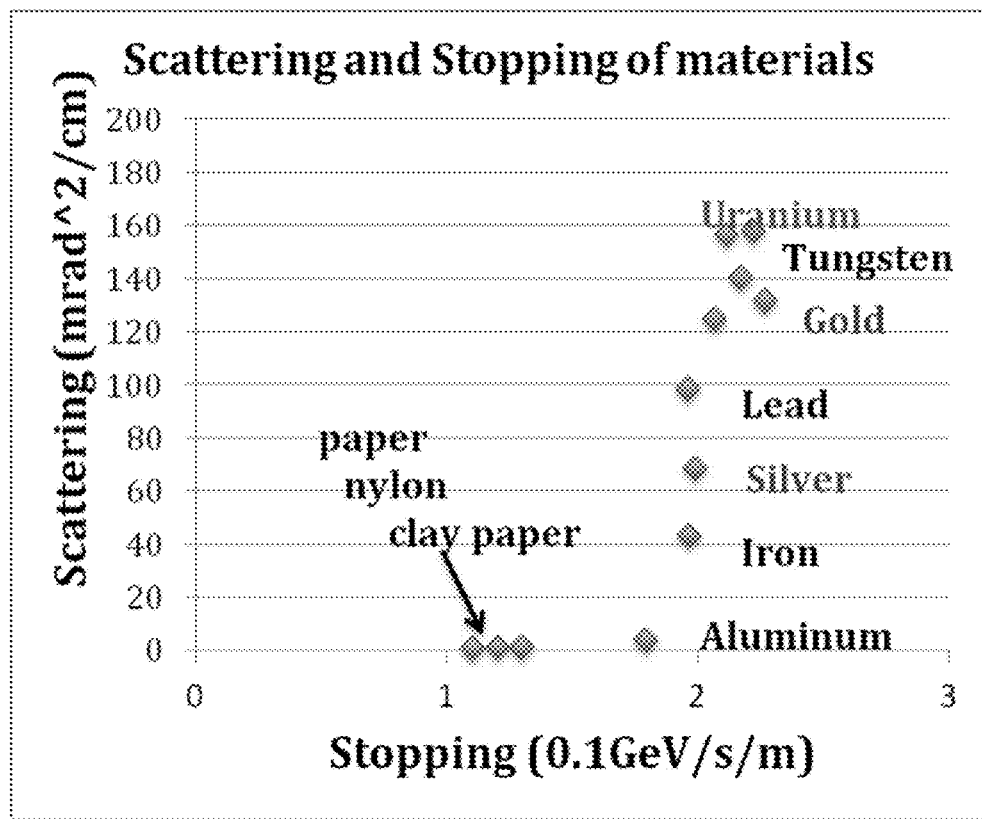
FIG. 11 shows exemplary results of simulations of cosmic ray electrons and muons incident on materials and elements.
Figure 12:
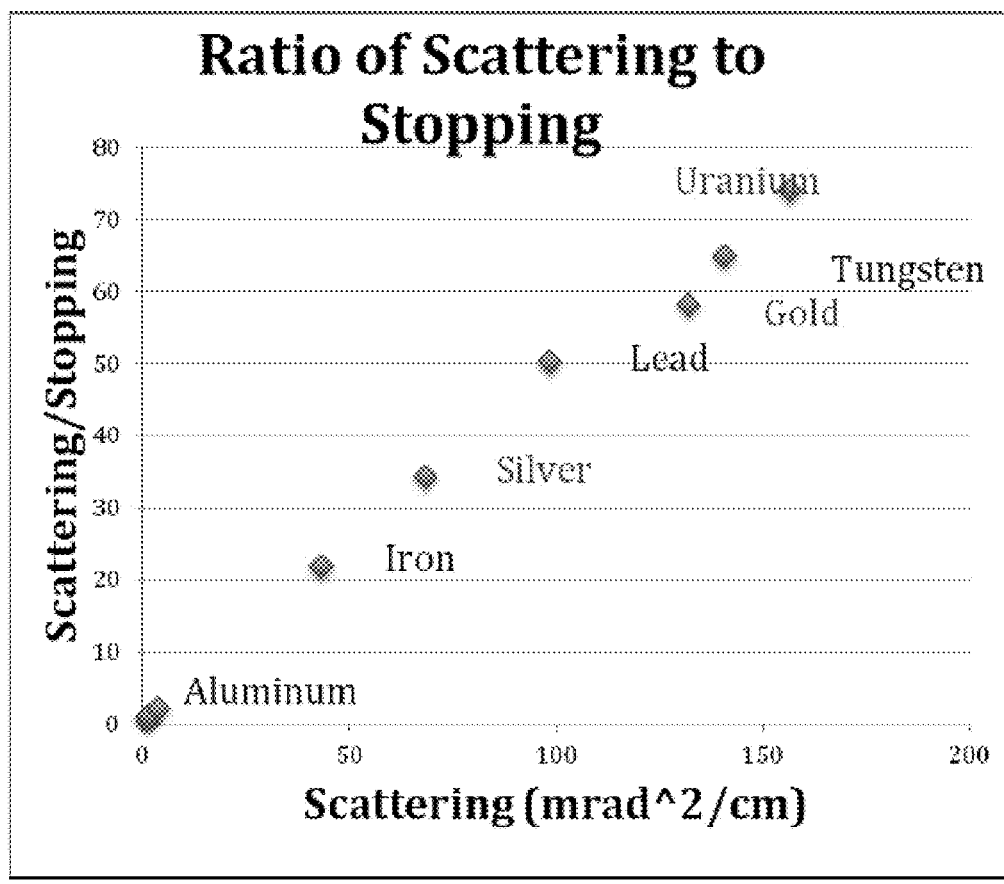
FIG. 12 shows the ratio of scattering to stopping, plotted against scattering.

FIG. 11 shows results of simulations of cosmic ray electrons and muons incident on materials and elements. The simulation's data were processed using standard algorithms to obtain scattering and stopping tracks. Simulated objects of medium and high density were 1 by 1 meter plates, 5.08 cm (2 inch) thick; the light objects were represented by 1 by 1 by 1 meter cubes. Objects were chosen to reduce geometry dependent (edge) effects. The data show two regimes. The low-density regime, comprising organic materials up to aluminum, is characterized by very little scattering but a strong variation in stopping power. The medium-to-high density regime shows a larger variation in scattering than in stopping power. Replotting the results of FIG. 11 exposes a new observation. FIG. 12 shows the ratio of scattering to stopping, plotted against scattering. It reveals an approximately linear relationship across the entire range of density and atomic mass. Ignoring geometric effects, it reveals a parameter, the scattering/stopping ratio.

Experimental Results

Data has been obtained for a wide range of materials from air (an empty container) to depleted uranium. The low-density regime, comprising materials up to aluminum, is characterized by very little scattering and a strong variation in stopping power. The medium-to-high density regime shows a larger variation in scattering than in stopping power. Practical implementation of the method needs further attention paid to geometric effects. For objects shaped like horizontal planes (sheets, slabs), essentially all the cosmic rays traverse the same thickness (or are stopped by the same thickness) as they penetrate the object. Objects whose horizontal extent is comparable to or smaller than their vertical thickness have a substantial number of particles with trajectories cutting through corners: that is, their path length is much shorter than that of particles heading through the entire thickness. This skews the observed scattering and stopping power. A more advanced implementation would utilize a reconstructed image of the scattering, then with image segmentation we can define the voxels that make up the sample and can compute the scattering and stopping by determining how many tracks went through one or more of the sample's voxels.

Figure 13:
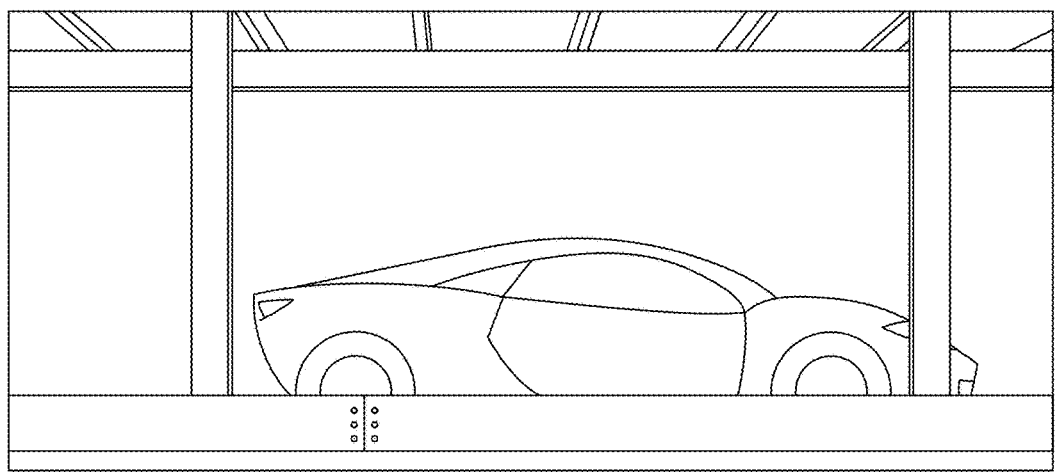
FIG. 13 shows a reconstructed image of a car loaded with materials.
Figure 14:
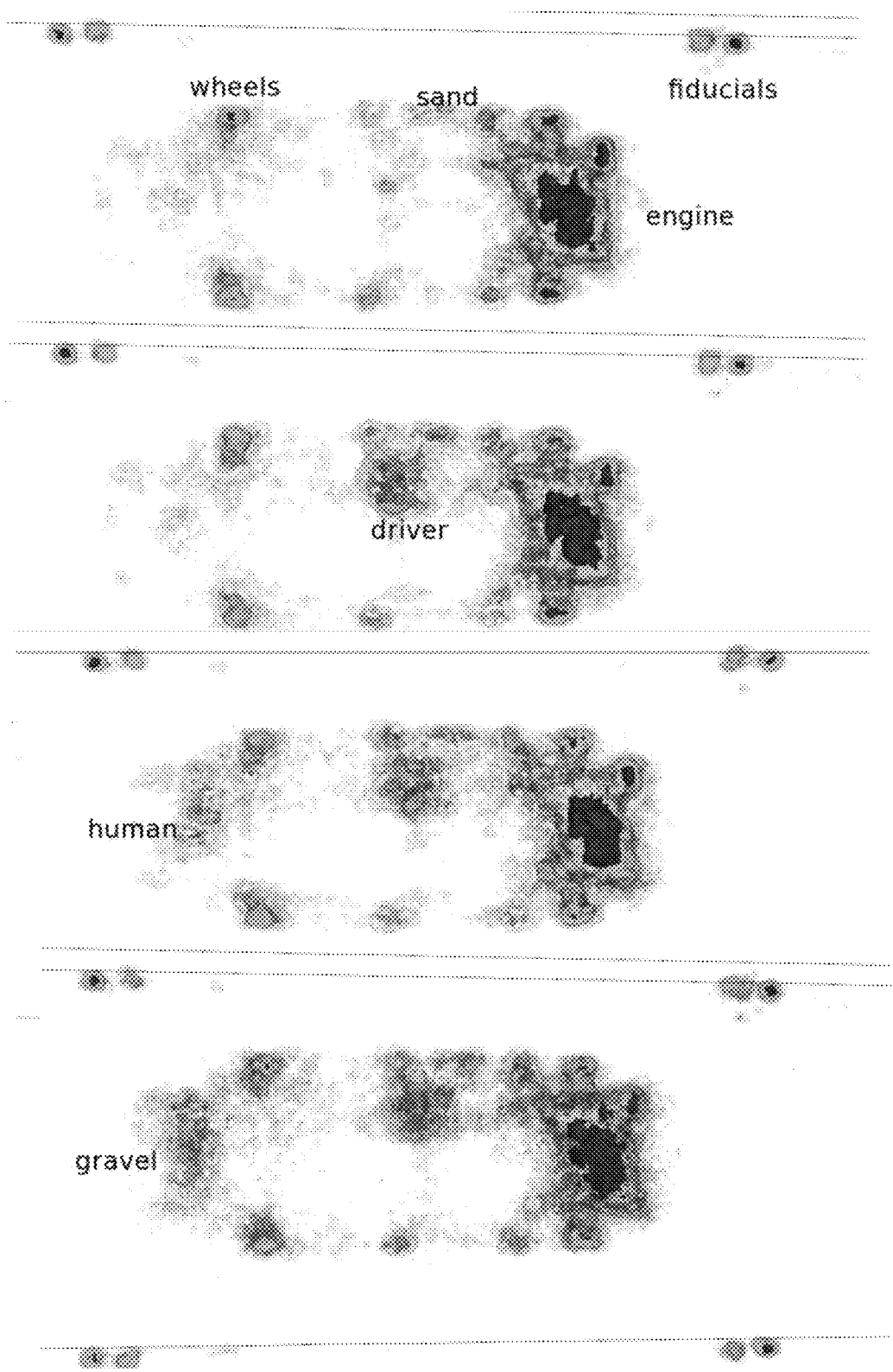
FIG. 14 shows reconstructions of four different scans of a car.

FIG. 13 shows a reconstructed images of a car loaded with materials. FIG. 14 shows reconstructions of four different scans of the car in the HMT. The top scan in FIG. 14 shows the car after sand was hidden in the driver's door. The next scan has a driver sitting in his seat. The third one has a driver and a person lying in the trunk. The last has a driver and gravel of about the same mass as the person in the third scan.

Referring back to FIG. 4, one finds the results of many scans of materials placed inside the trunk of the car. On the bottom left we see the lowest points for an empty detector and empty trunk which give a measure of the background signals due to the scattering and stopping in the detector elements and the car trunk area. The materials are spread out mostly towards the top right. The red squares are from simulations of explosives that were placed where they are predicted to lie.

Figure 15:
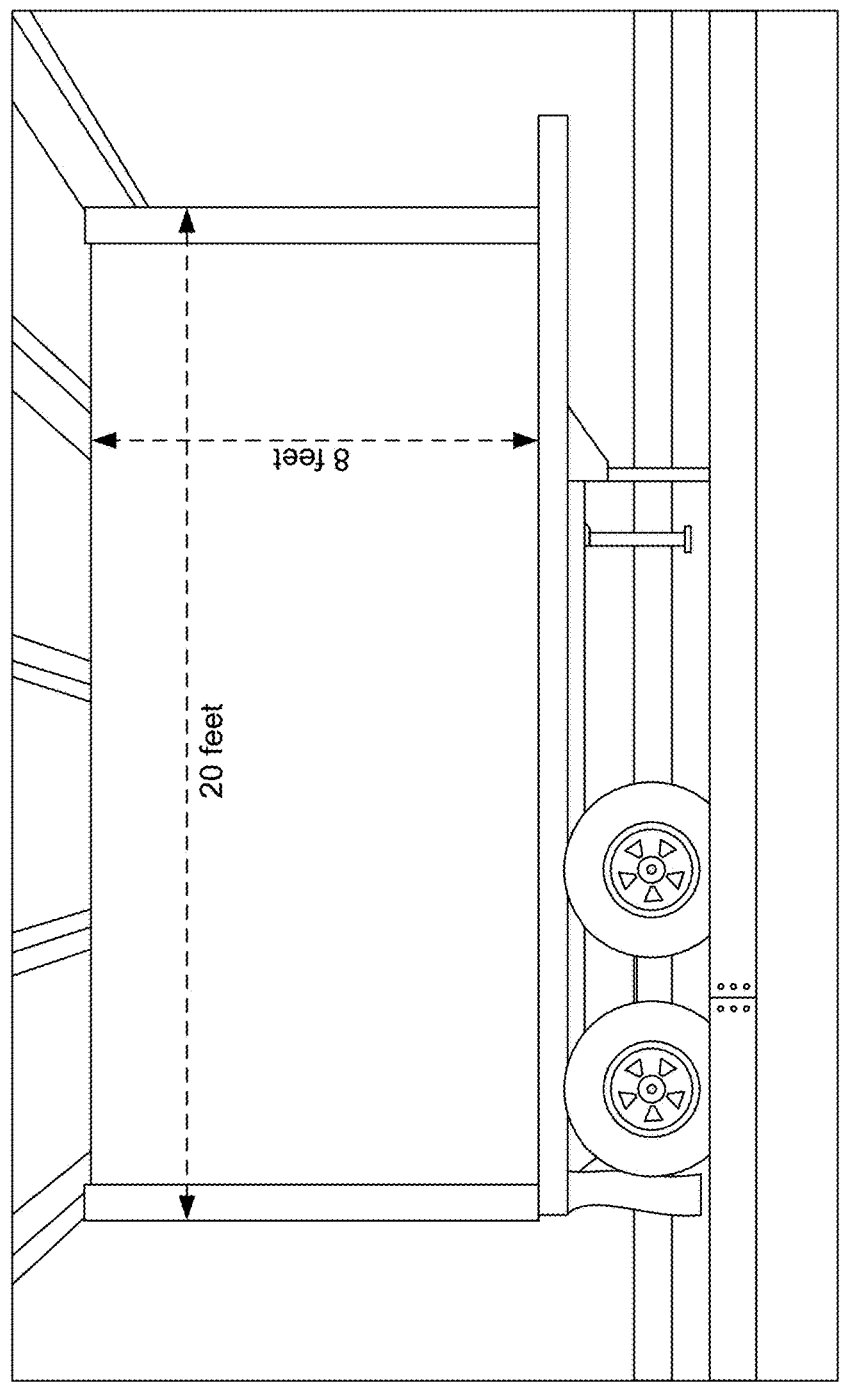
FIG. 15 shows a twenty foot container loaded with mostly pallet sized materials and scanned.
Figure 16:
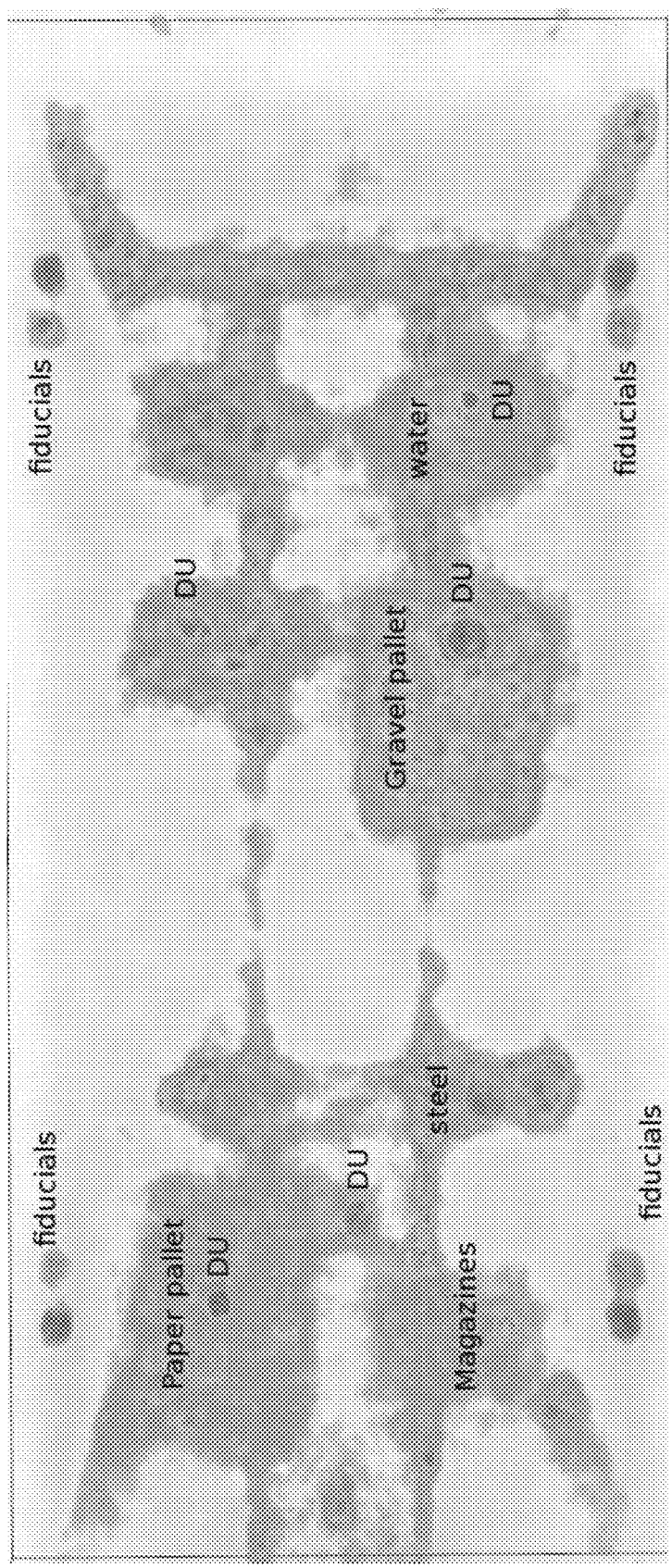
FIG. 16 shows an exemplary reconstruction of 20 foot container with pallets of paper, gravel, barrel of water, steel shelf and 5 SNM surrogates (DU) that vary from 2-20 kg.

FIG. 15 shows a twenty foot container loaded with mostly pallet sized materials and scanned in the HMT. An example of a reconstructed image is shown in FIG. 16. FIG. 16 shows an exemplary reconstruction of 20 foot container with pallets of paper, gravel, barrel of water, steel shelf and 5 SNM surrogates (DU) that vary from 2-20 kg.

Referring back to FIG. 3, one finds the results of many scans of materials placed inside the 20 foot container. FIG. 3 shows exemplary data from scans of materials placed in the 20 foot container. The red squares are simulations from explosives. On the bottom left we see the lowest point for an empty container which gives a measure of the background signals due to the scattering and stopping in the detector elements and the container. The materials are spread out mostly towards the top right. The red squares are from simulations of explosives that were placed according to a prediction.

Figure 17:
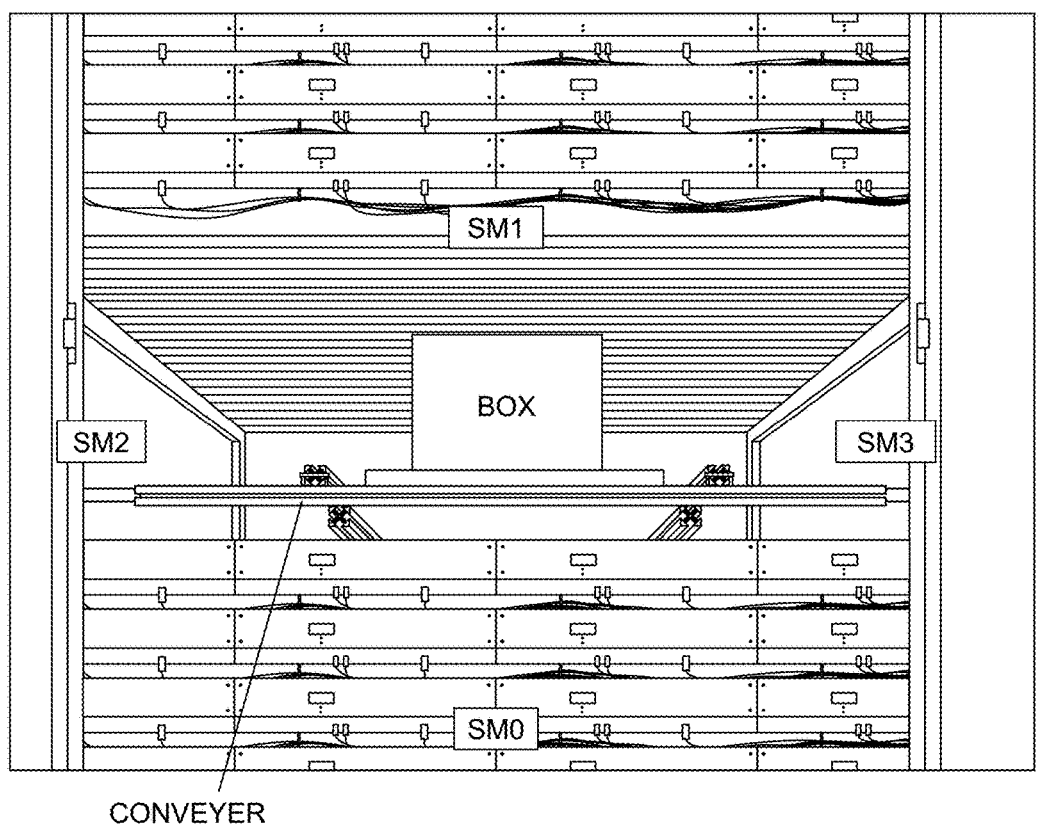
FIG. 17 shows an exemplary vehicle mountable sensor with six and eight foot drift tubes covering 4 sides.

The four sided package scanner being placed inside the deployment vehicle. The following data taken in Poway and at the Energetic Materials Research and Testing Center (EMRTC)10 of New Mexico Tech located in Socorro, N. Mex. were obtained without the side supermodules. FIG. 17 shows an exemplary vehicle mountable sensor with six and eight foot drift tubes covering 4 sides. Here it has a shipping container (BOX) on a conveyer.

Figure 18:
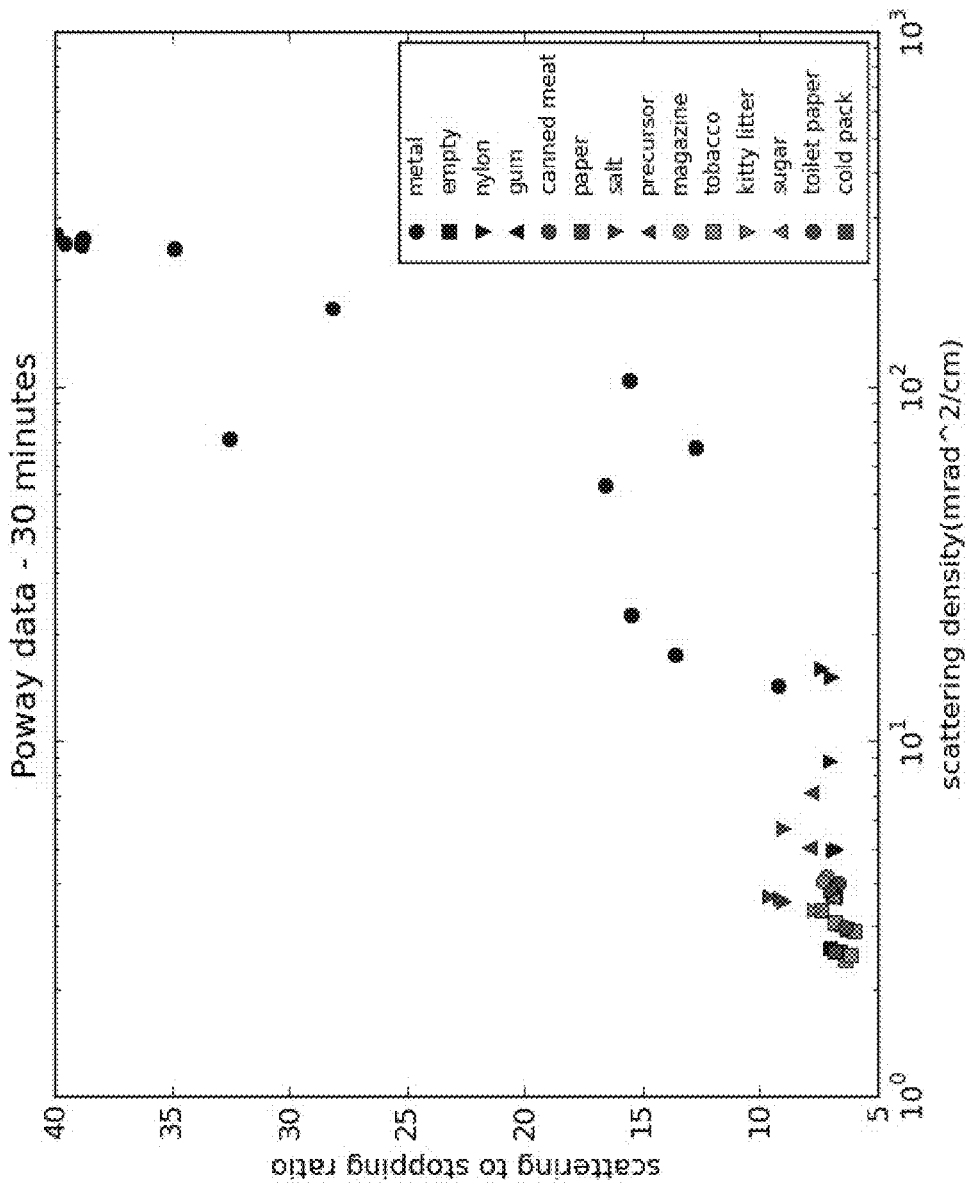
FIG. 18 shows exemplary ratio of scattering to stopping versus scattering for materials.

The data shown in FIG. 18 (30 minute scans) verify that the ratio of scattering to stopping that was described above is indeed useful as a classification feature for materials. The metals were mostly aluminum, steel and lead. The error bars are smaller than the points. FIG. 18 shows exemplary ratio of scattering to stopping versus scattering for materials.

Figure 19:
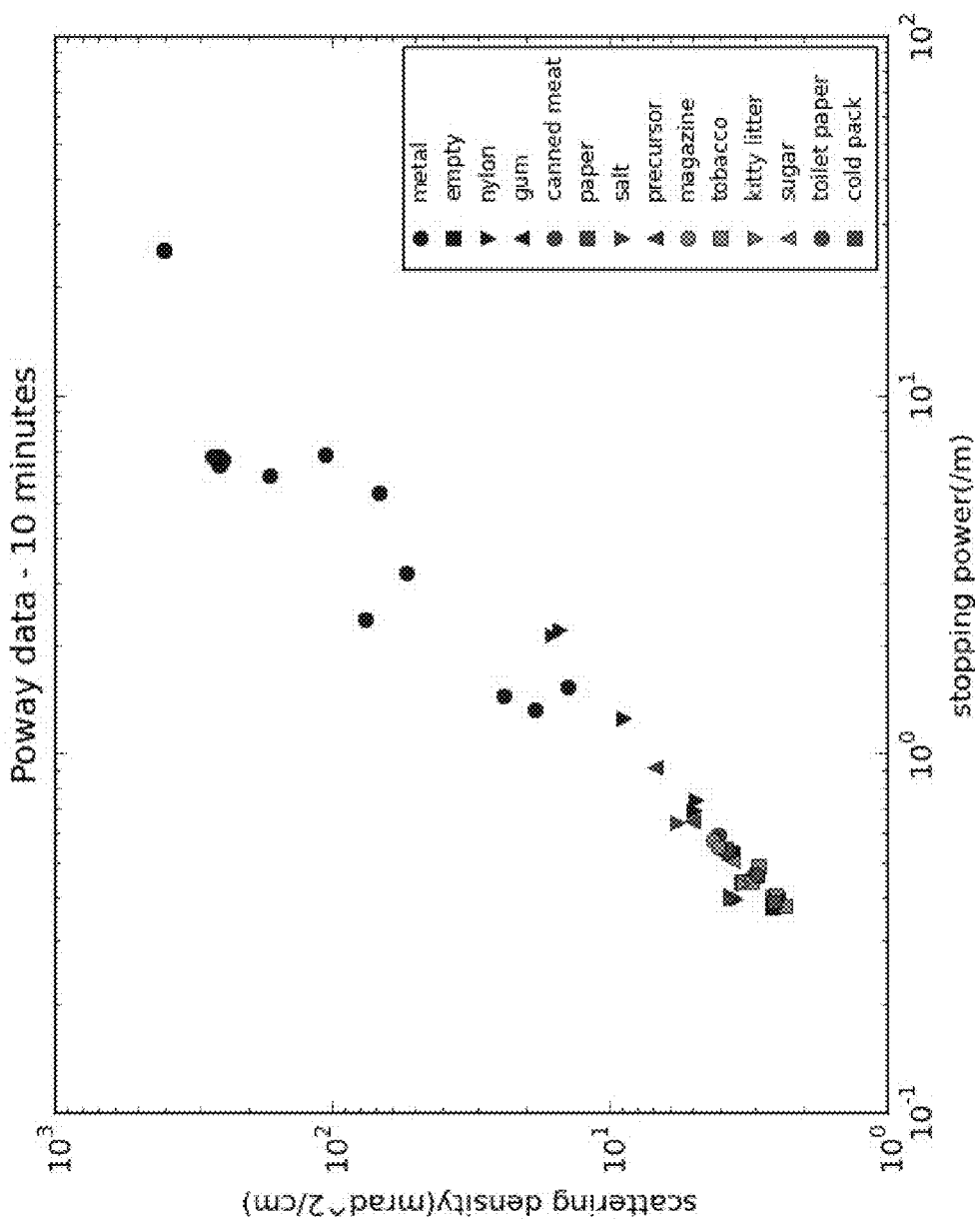
FIG. 19 shows exemplary scattering versus stopping for these materials.

In FIG. 19 we see the scattering versus stopping for these materials. Radioactive signals were detected in 4 materials that contained potassium. Since natural potassium contains a trace of radioactive K-40, the vehicle mountable sensor measured a clear gamma signal from these 4 materials and did not measure any activity over the low gamma threshold in the other scans. The normalized mass is the equivalent mass of only the potassium that is in each sample. The gamma intensity from the four salts shown in FIG. 16 might be expected to fall on a straight line starting at zero normalized mass. The fact that they do not is due to the variance in the density of the samples and their self-attenuation of the 1.46 MeV gamma rays that are emitted in the decay. Bromine has the highest attenuation coefficient, followed by chlorine and potassium. The densities were as follows: KBr (0.98 g/cc), $KClO_4$ (0.63 g/cc), and $KNO_3$ (1.23 g/cc) and KCl (1.08 g/cc).

Figure 20:
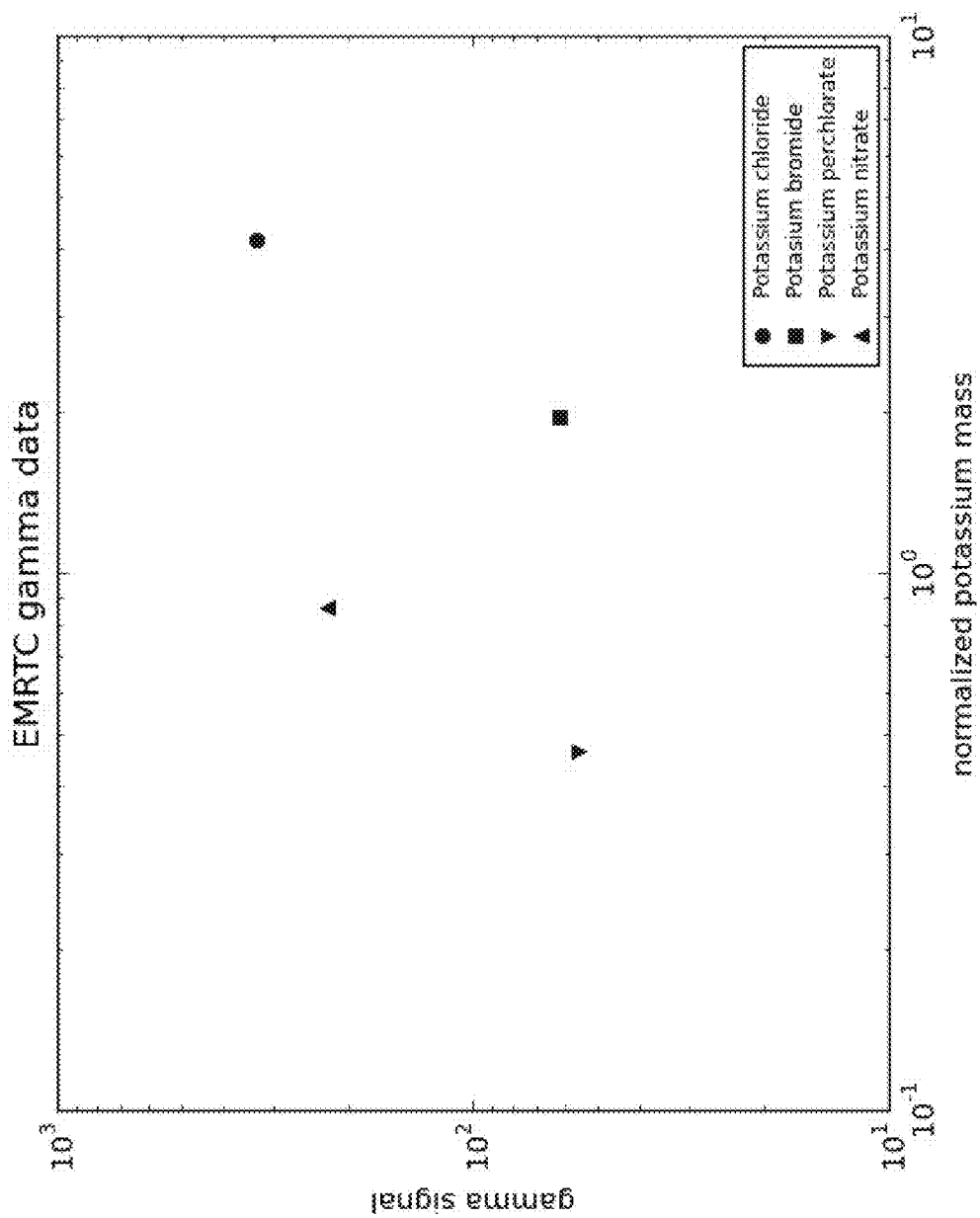
FIG. 20 shows gamma radiation signal detected in potassium salts as a function of normalized potassium mass (mass of the potassium component only).

FIG. 20 shows gamma radiation signal detected in potassium salts as a function of normalized potassium mass (mass of the potassium component only).

The disclosed technology shows that a scanner based upon passive radiation from cosmic ray particles as well as detection of emitted gamma rays is able to detect and classify a wide range of materials in reasonable timeframes. With image segmentation and the scattered and stopped tracks one can extract the scattering, the stopping, the ratio of scattering/stopping and the gamma signal as features for classification of detected objects. This is currently being investigated.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

Additional details are provided in the attached Appendix A and Appendix B, which form a part of the present document.

While this patent document and attached appendices contain many specifics, these should not be construed as limitations on the scope of any invention or of what may be claimed, but rather as descriptions of features that may be specific to particular embodiments of particular inventions. Certain features that are described in this patent document and attached appendices in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendices should not be understood as requiring such separation in all embodiments.

Only a few implementations and examples are described and other implementations, enhancements and variations can be made based on what is described and illustrated in this patent document.

What is claimed is:

1. A method for identifying a scattering-stopping relationship for a range of low-density materials exposed to cosmic-ray charged particles, the method comprising:
exposing, at a charge particle detection system, the range of low-density materials located within a volume of interest (VOI) to cosmic ray charged particles including cosmic-ray muons and cosmic-ray electrons;
determining a scattering number associated with a subset of the exposed cosmic ray charged particles entering the VOI, interacting with the range of low-density materials located within the VOI, and exiting the VOI;
determining a raw stopping number associated with a subset of the exposed cosmic ray charged particles entering the VOI, interacting with the range of low-density materials within the VOI, and stopping inside the VOI; and
determining, based at least partly on a scattering signal and a stopping power, a scattering-stopping ratio that enables a classification of the range of low-density materials,
wherein the scattering signal is expressed in terms of a scattering angle of the subset of the exposed cosmic ray charged particles entering the VOI, interacting with the range of low-density materials located within the VOI, and exiting the VOI, a momentum of the cosmic ray charged particles, and a dimension of the VOI,
wherein the stopping power is expressed in terms of the scattering number, the raw stopping number, the momentum of the cosmic ray charged particles, and the dimension of the VOI, and
wherein the cosmic-ray electrons demonstrate greater scattering responses than the cosmic-ray muons in materials having low-atomic-mass elements and greater stopping responses than the cosmic-ray muons in materials having medium-atomic-mass elements such that combining scattering and stopping responses of the cosmic-ray electrons and the cosmic-ray muons enables a classification of materials that is extended beyond Special Nuclear Materials.

2. The method of claim 1, wherein the exposing, determining the scattering number, determining the raw stopping number, and determining the scattering-stopping ratio are performed for the range of low-density materials one material at a time.

3. The method of claim 1, further comprises: determining an effect of a container defining the VOI by separately measuring a scattering signal and a stopping power associated with the container empty.

4. The method of claim 1, wherein at least one material in the range of low-density materials has a density below 3 g/cc.

5. The method of claim 1, wherein values of the scattering signal and stopping power increase with densities of the range of low-density materials.

6. The method of claim 1, wherein determining the scattering number includes:
detecting, from a first set of position sensitive cosmic ray charged particle detectors of the charged particle detection system, events of incident charge particles from the exposed cosmic ray charged particles that penetrate the first set of position sensitive cosmic ray charged particle detectors and enter the VOI;
detecting, from a second set of position sensitive cosmic ray charged particle detectors of the charged particle detection system, events of outgoing charged particles from the exposed cosmic ray charged particles exiting the VOI;
receiving, at a signal processing unit of the charged particle detection system, signals associated with the events of the incident cosmic ray charged particles from the first set of position sensitive cosmic ray charged particle detectors and signals associated with events of the outgoing cosmic ray charged particles from the second set of position sensitive cosmic ray charged particle detectors; and
determining, by the signal processing unit, the scattering number based at least on the received signals associated with the events of the outgoing cosmic ray charged particles from the second set of position sensitive cosmic ray charged particle detectors.

7. The method of claim 6, wherein determining the raw stopping number associated with a subset of the exposed cosmic ray charged particles interacting with the VOI includes:
using received signals associated with the events of the incident cosmic ray charged particles from the first set of position sensitive cosmic ray charged particle detectors to determine a number of the incident cosmic ray charged particles and using received signals associated with the events of the outgoing cosmic ray charged particles from the second set of position sensitive cosmic ray charged particle detectors to determine a number of scattered cosmic ray charged particles; and
computing the raw stopping number of stopped cosmic ray charged particles by subtracting the number of scattered cosmic ray charged particles from the number of incident cosmic ray charged particles.

8. The method of claim 7, wherein the stopping power is normalized by dividing the raw stopping number of stopped cosmic ray charged particles by the scattering number to account for variations in detection efficiency at different locations of the cosmic ray detector.

9. The method of claim 7, further comprising correcting the raw stopping number of stopped cosmic ray charged particles to compensate for effects of a thickness of the VOI.

10. The method of claim 6, wherein the method further comprises correcting the scattering signal and stopping power to compensate for a geometric effect of the VOI.

11. A method for identifying contents of a volume of interest (VOI) exposed to cosmic ray charged particles, the method comprising:
determining, by a charged particle detection system, a number of scattered cosmic ray charged particles from cosmic-ray charged particles that include cosmic-ray muons and cosmic-ray electrons interacting with the VOI;
determining a number of stopped cosmic ray charged particles from the cosmic ray charged particles that include the cosmic-ray muons and the cosmic-ray electrons interacting with the VOI;
determining, based at least partly on a scattering signal and a stopping power, a scattering-stopping ratio; and
comparing the scattering-stopping ratio against a predetermined set of scattering-stopping ratios for a range of low-density materials to determine whether the contents of the VOI match a material in the range of low-density materials to enable a classification of the contents of the VOI, wherein the scattering signal is expressed in terms of a scattering angle of the scattered cosmic ray charged particles, a momentum of the cosmic ray charged particles, and a dimension of the VOI, wherein the stopping power is expressed in terms of the number of stopped cosmic ray charged particles, the momentum of the cosmic ray charged particles, the number of scattered cosmic ray charged particles, and the dimension of the VOI, and wherein the cosmic-ray electrons demonstrate greater scattering responses than the cosmic-ray muons in materials having low-atomic-mass elements and greater stopping responses than the cosmic-ray muons in materials having medium-atomic-mass elements such that combining scattering and stopping responses of the cosmic-ray electrons and the cosmic-ray muons enables the classification of the contents of the VOI that is extended beyond Special Nuclear Materials.

12. The method of claim 11, wherein the VOI is exposed to the cosmic ray charged particles from inside a container.

13. The method of claim 12, wherein the container includes a shipping container, a vehicle, or, a package.

14. The method of claim 12, wherein the method further comprises correcting the numbers of scattered and stopped cosmic ray charged particles for an effect of the container.

15. The method of claim 11, wherein determining the number of scattered cosmic ray charged particles from cosmic ray charged particles interacting with the VOI includes:

detecting, by a first set of position sensitive cosmic ray charged particle detectors of the charged particle detection system, events of incident cosmic ray charged particles that penetrate the first set of position sensitive cosmic ray charged particle detectors and enter the VOI;

detecting by a second set of position sensitive cosmic ray charged particle detectors of the charged particle detection system, events of outgoing cosmic ray charged particles exiting the VOI;

receiving, at a signal processing unit of the detection system, signals associated with the events of the incident cosmic ray charged particles from the first set of position sensitive cosmic ray charged particle detectors and signals associated with the events of the outgoing cosmic ray charged particles from the second set of position sensitive cosmic ray charged particle detectors; and determining, by the signal processing unit, a number of the scattered cosmic ray charged particles based at least on the received signals associated with the events of the outgoing cosmic ray charged particles.

16. The method of claim 15, wherein determining the number of stopped cosmic ray charged particles from cosmic ray charged particles interacting with the VOI includes:

determining a number of the incident cosmic ray charged particles based on the received signals associated with the events of the incident cosmic ray charged particles from the first set of position sensitive cosmic ray charged particle detectors; and computing a raw number of stopped cosmic ray charged particles by subtracting the determined number of scattered cosmic ray charged particles from the determined number of the incident cosmic ray charged particles.

17. The method of claim 16, wherein the stopping power of the stopped cosmic ray charged particles is normalized by dividing the raw number of the stopped cosmic ray charged particles by the number of the scattered cosmic ray charged particles to compensate for effects of a placement location of the VOI inside the cosmic ray detector.

18. The method of claim 16, further comprising correcting the raw number of the stopped cosmic ray charged particles to compensate for effects of a thickness of the VOI.

19. The method of claim 11, wherein the method further comprises correcting the numbers of the scattered and stopped cosmic ray charged particles to compensate for a geometric effect of the VOI.

20. The method of claim 11, wherein the method further comprises using the number of the stopped cosmic ray charged particles to estimate a thickness of the VOI.

21. The method of claim 11, wherein the method further comprises classifying the contents of the VOI as a low density material when the scattering-stopping ratio falls within a range of the predetermined set of scattering-stopping ratios for the range of low-density materials.

22. A charged particle detection unit for detecting a material in a volume of interest (VOI) exposed to cosmic-ray charged particles, comprising:

a first set of position sensitive cosmic ray charged particle detectors to detect events of incident cosmic ray charged particles that penetrate the first set of position sensitive cosmic ray charged particle detectors and enter the VOI, wherein the incident cosmic ray charged particles include cosmic-ray muons and cosmic-ray electrons;

a second set of position sensitive cosmic ray charged particle detectors to detect events of outgoing cosmic ray charged particles exiting the VOI; and a signal processing unit to receive signals associated with the events of the incident cosmic ray charged particles from the first set of position sensitive cosmic ray charged particle detectors and signals associated with the events of the outgoing cosmic ray charged particles from the second set of position sensitive cosmic ray charged particle detectors, wherein the signal processing unit is configured to determine, based at least partly on a scattering signal and a stopping power, a scattering-stopping ratio for the material to enable a classification of the material by obtaining a number of scattered cosmic ray charged particles and a raw number of stopped cosmic ray charged particles in the VOI based on the received signals associated with the events of the incident cosmic ray charged particles and the outgoing cosmic ray charged particles, wherein the scattering signal is expressed in terms of a scattering angle of the scattered cosmic ray charged particles, a momentum of the cosmic ray charged particles, and a dimension of the VOI, wherein the stopping power is expressed in terms of the raw number of stopped cosmic ray charged particles, the momentum of the cosmic ray charged particles, the number of scattered cosmic ray charged particles, and the dimension of the VOI, and wherein the cosmic-ray electrons demonstrate greater scattering responses than the cosmic-ray muons in materials having low-atomic-mass elements and greater stopping responses than the cosmic-ray muons in materials having medium-atomic-mass elements such that combining scattering and stopping responses of the cosmic-ray electrons and the cosmic-ray muons enables a classification of materials that is extended beyond Special Nuclear Materials.

23. The detection unit of claim 22, wherein the signal processing unit is configured to:
- determine a number of the incident cosmic ray charged particles based on the received signals associated with the events of the incident charged particles from the first set of position sensitive cosmic ray charged particle detectors;
- determine the number of the scattered cosmic ray charged particles based on the received signals associated with the events of the outgoing cosmic ray charged particles from the second set of position sensitive cosmic ray charged particle detectors; and
- compute the raw number of the stopped cosmic ray charged particles by subtracting the determined number of the scattered cosmic ray charged particles from the determined number of the incident cosmic ray charged particles.

24. The detection unit of claim 22, wherein the first set and second set of position sensitive cosmic ray charged particle detectors includes a set of drift tubes.

25. The detection unit of claim 22, wherein the first set and second set of position sensitive cosmic ray charged particle detectors includes a set of drift tubes which can be used to detect both cosmic-ray muons and cosmic-ray electrons.

* * * * *